(12) United States Patent
Poo et al.

(10) Patent No.: US 9,687,241 B1
(45) Date of Patent: Jun. 27, 2017

(54) LINEAR ANASTOMOSIS CLAMP AND STAPLER

(71) Applicants: Biorep Technologies, Inc., Miami Lakes, FL (US); Zakease Surgical, Inc., Miami, FL (US)

(72) Inventors: Ramon E. Poo, Miami, FL (US); Andreas G. Tzakis, Miami, FL (US)

(73) Assignees: ZAKEASE SURGICAL, INC., Miami, FL (US); BIOREP TECHNOLOGIES, INC., Miami Lakes, FL (US)

( * ) Notice: Subject to any disclaimer, the term of this patent is extended or adjusted under 35 U.S.C. 154(b) by 0 days.

(21) Appl. No.: 15/267,495

(22) Filed: Sep. 16, 2016

(51) Int. Cl.
*A61B 17/068* (2006.01)
*A61B 17/115* (2006.01)
*A61B 17/072* (2006.01)
*A61B 17/00* (2006.01)

(52) U.S. Cl.
CPC .......... *A61B 17/115* (2013.01); *A61B 17/072* (2013.01); *A61B 17/07207* (2013.01); *A61B 2017/00818* (2013.01); *A61B 2017/07257* (2013.01); *A61B 2017/07271* (2013.01)

(58) Field of Classification Search
CPC . A61B 17/072; A61B 17/1114; A61B 17/115; A61B 2017/00818; A61B 2017/1125
See application file for complete search history.

(56) References Cited

U.S. PATENT DOCUMENTS

| 3,144,654 | A | * | 8/1964 | Mallina | A61B 17/1152 227/19 |
| 3,973,709 | A | * | 8/1976 | Akopov | A61B 17/1152 227/19 |
| 4,216,890 | A | * | 8/1980 | Akopov | A61B 17/07207 227/19 |
| 4,466,436 | A | * | 8/1984 | Lee | A61B 17/1152 227/179.1 |
| 4,821,939 | A | * | 4/1989 | Green | A61B 17/072 227/19 |
| 5,242,457 | A | * | 9/1993 | Akopov | A61B 17/064 227/175.1 |
| 5,490,856 | A | * | 2/1996 | Person | A61B 17/072 227/175.1 |
| 5,551,622 | A | * | 9/1996 | Yoon | A61B 17/072 227/176.1 |
| 5,662,260 | A | * | 9/1997 | Yoon | A61B 17/072 227/176.1 |

(Continued)

*Primary Examiner* — Andrew M Tecco
(74) *Attorney, Agent, or Firm* — Fox Rothschild LLP

(57) ABSTRACT

An anastomosis device includes a stapler and an anvil. The stapler includes a clamp head with opposing first and second clamp jaws and a clamp actuator and clamp lock. Staple magazines are connected to the clamp jaws for retaining a plurality of staples in an array, and drivers are provided for moving the plurality of staples in the array out of the staple magazine. An anvil includes a clamp head with opposing first and second clamp jaws, a clamp actuator and a clamp lock. Anvil portions are connected to the clamp jaws. The stapler detachably engages to the anvil, and aligns the staple magazines with the anvils. The drivers are operated to move the staples from the staple magazines into contact with the anvil portions. A method for performing anastomosis is also disclosed.

17 Claims, 34 Drawing Sheets

(56) References Cited

U.S. PATENT DOCUMENTS

| | | | | |
|---|---|---|---|---|
| 8,245,897 B2* | 8/2012 | Tzakis | ............... | A61B 17/1152 227/175.1 |
| 8,448,833 B2* | 5/2013 | Tzakis | ................. | A61B 17/115 227/181.1 |
| 2011/0180584 A1* | 7/2011 | Tzakis | ................. | A61B 17/115 227/175.1 |
| 2011/0184443 A1* | 7/2011 | Tzakis | ............... | A61B 17/1152 606/153 |

* cited by examiner

LINEAR ANASTOMOSIS CLAMP AND STAPLER

FIELD OF THE INVENTION

The present invention is directed to anastomosis, and more particularly to anastomosis staplers.

BACKGROUND OF THE INVENTION

Anastomosis is a surgical term for describing the joining of two hollow bodies, particularly blood and lymphatic vessels. Anastomosis can be end-to-end, as when the ends of a severed or damaged vessel are rejoined, or end-to-side, as when an end of a vessel is joined to the side of another vessel or hollow structure. The primary method for surgically anastomosing vessel ends has been the circumferential suture, in which a suture is hand applied around the ends of the two vessels. Circumferential suturing is a time-consuming, exacting process. It is very important that the ends of the vessels be joined properly, as leakage or obstruction of the vessel lumen is possible, with potential serious effects on the patient's health. The physical manipulation of the vessel that is necessary for circumferential suturing can also result in damage to the vessel ends, with resulting degradation of the anastomosed vessel.

Various mechanical methods have been proposed for performing end-to-end anastomosis without circumferential suturing. One such anastomosis system and method is described in Poo et al. U.S. Pat. Nos. 8,348,128 and 8,777,084, which describes a circumferential anastomosis device. Anastomosis of vessels requires clamping the vessels during the anastomosis procedure. The inclusion of vessel clamps alongside anastomosis devices is limited by the space available in the surgical environment. In some forms of surgery, space for clamps and anastomosis devices is extremely limited.

SUMMARY OF THE INVENTION

An anastomosis device includes a stapler and an anvil. The stapler includes a clamp head with opposing first and second clamp jaws and a clamp actuator for moving the opposing jaws toward one another to a clamping position. A lock secures the clamp jaws in the clamping position. The stapler can include a handle and the anvil can include a handle.

A first staple magazine is connected to the first clamp jaw for retaining a plurality of staples in an array. A first driver associated with the first staple magazine is provided for simultaneously moving the plurality of staples in the array out of the staple magazine. A second staple magazine is connected to the second clamp jaw for retaining a plurality of staples in an array. A second driver associated with the second staple magazine is provided for simultaneously moving the plurality of staples in the array out of the staple magazine.

The anvil includes a clamp head with opposing first and second clamp jaws and a clamp actuator for moving the opposing jaws toward one another to a clamping position. A lock secures the clamp jaws in the clamping position. A first anvil portion is connected to the first clamp jaw, and a second anvil portion is connected to the second clamp jaw.

Engagement structure on the stapler and the anvil detachably engages the stapler to the anvil, whereupon the first anvil portion will be positioned adjacent to and aligned with the first staple magazine and the second anvil portion will be positioned adjacent to and aligned with the second staple magazine. The first driver associated with the first staple magazine can be operated to simultaneously move the plurality of staples from the first staple magazine into contact with the first anvil portion. The second driver associated with the second staple magazine can be operated to simultaneously move the plurality of staples from the second staple magazine into contact with the second anvil portion.

The first driver associated with the first staple magazine can be connected to a first lever for operating the first driver, and the second driver associated with the second staple magazine can be connected to a second lever for operating the second driver.

A movable staple piston can have a plurality of staple seats for contacting and retaining the staples. The first driver and second driver can include a staple plunger. The staple piston can be contacted and moved by the staple plunger upon operation of the levers to move the staple seats and the staples. The staples will thereby be driven from the staple magazine. The first staple magazine and second staple magazine can include staple channels for each staple in the array to retain and direct the staples as they are driven from the staple magazine.

The first anvil portion and second anvil portion can include staple anvil subportions for alignment with each of the plurality of staples in the staple array. The staples are driven towards the anvil, and the anvil subportions will direct ends of the staples inward and rearward to close the staples and secure the vessel ends together.

Each of the first clamp jaw and second clamp jaw of the stapler and first clamp jaw and second clamp jaw of the anvil can include tissue flap retaining members. The tissue flap retaining members can be spring loaded to urge the retaining member toward the respective clamp jaw.

The engagement structure can be cooperating ball and socket members on distal ends of the first clamp jaw of the stapler and first clamp jaw of the anvil, and cooperating ball and socket members on the second clamp jaw of the stapler and second clamp jaw of the anvil. The engagement structure can be adjustable to permit changes in the spacing between the first staple magazine and first anvil portion, and between the second staple magazine and the second anvil portion.

The anastomosis device can further include proximal engagement structure for engaging the stapler to the anvil. The engagement structure can include a latch on one of the stapler and the anvil, and a cooperating keeper on the other of the stapler and the anvil.

The lock for securing the clamp jaws of the stapler and the lock for securing the clamp jaws of the anvil in the clamping position can be of many different constructions. In one embodiment, the lock can comprise a ratchet.

The staple array can be any suitable array. The staple array can be a linear array. The staple array can include at least two rows.

A method of performing anastomosis device can include the step of providing a stapler. The stapler can include a clamp head with opposing first and second clamp jaws and a clamp actuator for moving the opposing jaws toward one another to a clamping position, a lock for securing the clamp jaws in the clamping position, a first staple magazine connected to the first clamp jaw for retaining a plurality of staples in an array, and a first driver associated with the first staple magazine for simultaneously moving the plurality of staples in the array out of the staple magazine and a second staple magazine connected to the second clamp jaw for retaining a plurality of staples in an array, and a second driver associated with the second staple magazine for simultaneously moving the plurality of staples in the array out of the staple magazine.

The method can further include the step of providing an anvil. The anvil can include a clamp head with opposing first and second clamp jaws and a clamp actuator for moving the opposing jaws toward one another to a clamping position, a lock for securing the clamp jaws in the clamping position, a first anvil portion connected to the first clamp jaw, and a second anvil portion connected to the second clamp jaw. Engagement structure can be provided on the stapler and the anvil for detachable engagement of the stapler to the anvil.

The method further includes the step of positioning the first anvil portion adjacent to and aligned with the first staple magazine and positioning the second anvil portion adjacent to and aligned with the second staple magazine. The method includes the step of operating the first driver associated with the first staple magazine to move the plurality of staples from the first staple magazine into contact with the first anvil portion, and operating the second driver associated with the second staple magazine to move the plurality of staples from the second staple magazine into contact with the second anvil portion.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
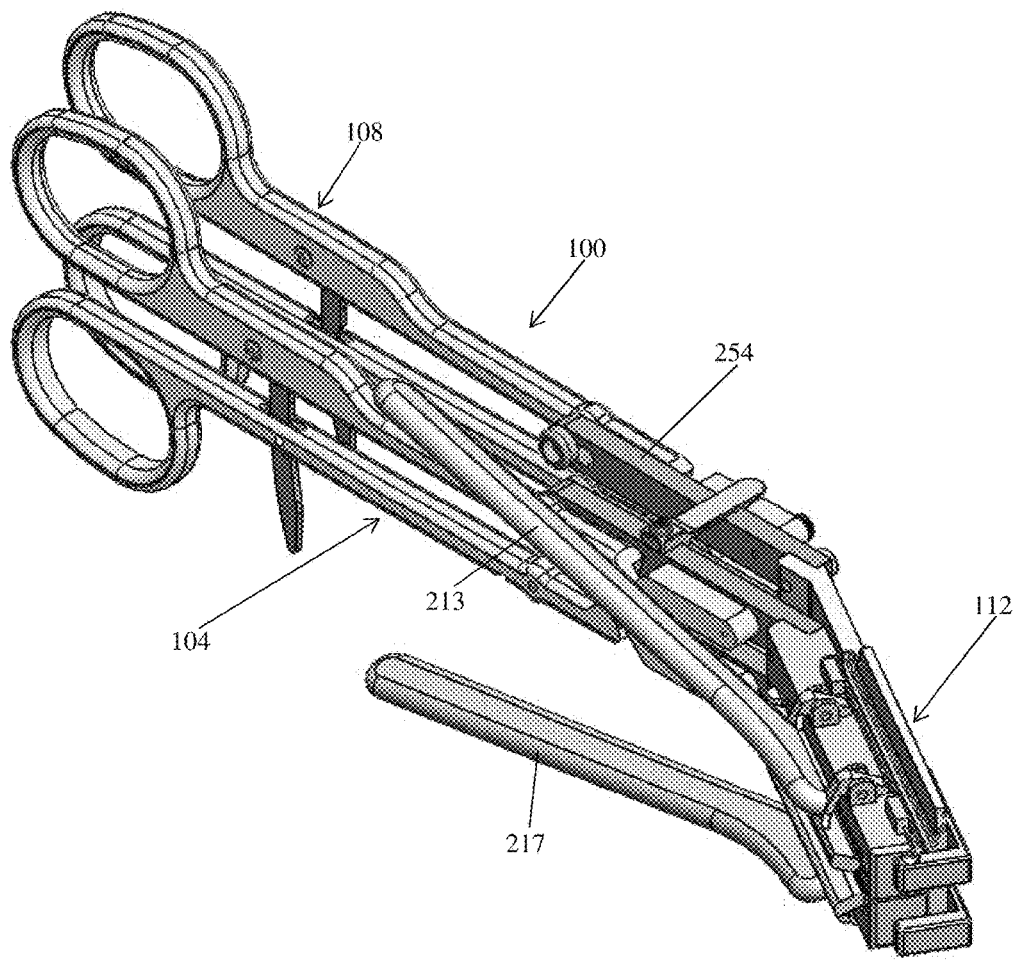
FIG. 1 is a top perspective view of a linear anastomosis clamp and stapler according to the invention.
Figure 2:
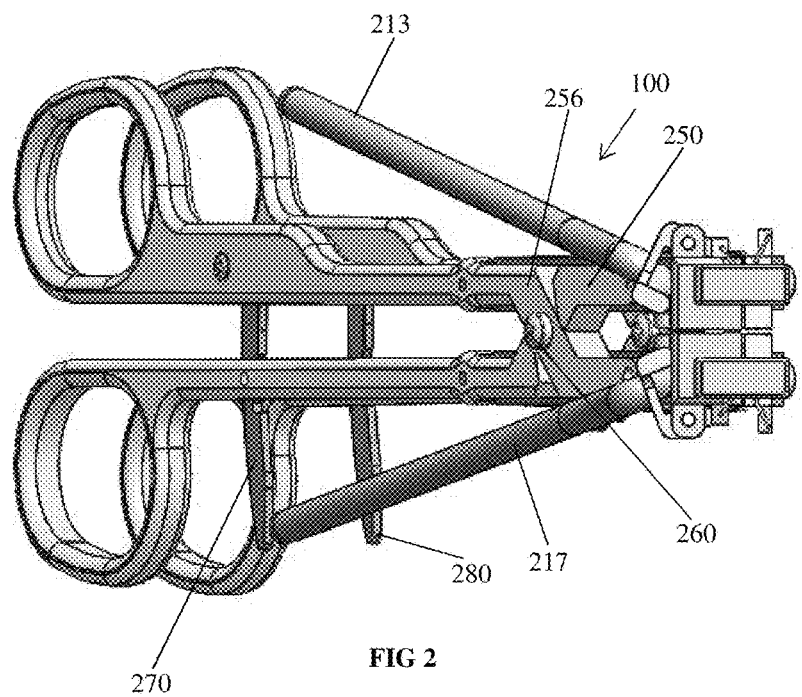
FIG. 2 is a front perspective.
Figure 3:
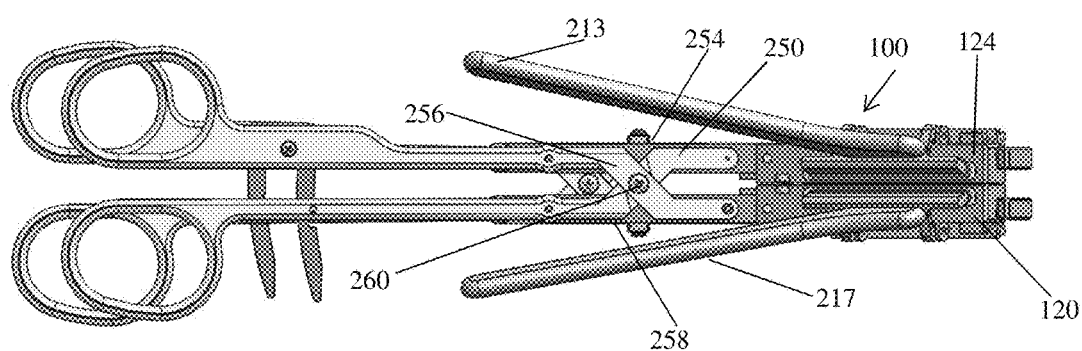
FIG. 3 is a first side elevation.
Figure 4:
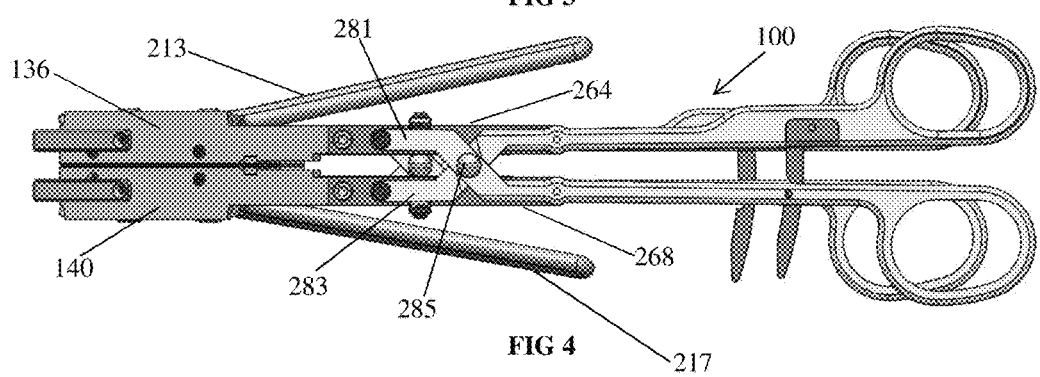
FIG. 4 is an opposite side elevation.

An anastomosis and clamp device includes a stapler and an anvil. The stapler includes a clamp head with opposing first and second clamp jaws and a clamp actuator for moving the opposing jaws toward one another to a clamping position. A lock secures the clamp jaws in the clamping position. The stapler can include a handle and the anvil can include a handle.

A first staple magazine can be connected to the first clamp jaw of the stapler for retaining a plurality of staples in an array. A first driver associated with the first staple magazine is provided for simultaneously moving the plurality of staples in the array out of the staple magazine. A second staple magazine is connected to the second clamp jaw of the stapler for retaining a plurality of staples in an array. A second driver associated with the second staple magazine is provided for simultaneously moving the plurality of staples in the array out of the second staple magazine.

An anvil includes a clamp head with opposing first and second clamp jaws and a clamp actuator for moving the opposing jaws toward one another to a clamping position. A lock can secure the clamp jaws in the clamping position. A first anvil portion is connected to the first clamp jaw, and a second anvil portion is connected to the second clamp jaw.

Engagement structure on the stapler and the anvil detachably engages the stapler to the anvil, whereupon the first anvil portion will be positioned adjacent to and aligned with the first staple magazine and the second anvil portion will be positioned adjacent to and aligned with the second staple magazine. The engagement structure can include cooperating engagement structure at distal ends of the stapler and the anvil. Any suitable engagement structure can be used.

The first driver associated with the first staple magazine can be operated to simultaneously move the plurality of staples from the first staple magazine into contact with the first anvil portion. The second driver associated with the second staple magazine can be operated to simultaneously move the plurality of staples from the second staple magazine into contact with the second anvil portion.

The first driver associated with the first staple magazine can be connected to a first lever for operating the first driver, and the second driver associated with the second staple magazine can be connected to a second lever for operating the second driver.

A movable staple piston can have a plurality of staple seats for contacting and retaining the staples. The first driver and second driver can include a staple plunger. The staple piston can be contacted and moved by the staple plunger upon operation of the levers to move the staple seats and the staples. The staples will thereby be driven from the staple magazine. The first staple magazine and second staple magazine can include staple channels for each staple in the array to retain and direct the staples as they are driven from the staple magazine.

The first anvil portion and second anvil portion can include staple anvil subportions for alignment with each of the plurality of staples in the staple array. The staples are driven towards the anvil, and the anvil portions will direct ends of the staples inward or outward and rearward to bend the staple ends and secure the vessel ends together.

Each of the first clamp jaw and second clamp jaw of the stapler and first clamp jaw and second clamp jaw of the anvil can include tissue flap retaining members. The tissue flap retaining members can be spring loaded to urge the retaining member toward the respective clamp jaw.

The engagement structure can be cooperating ball and socket members on distal ends of the first clamp jaw of the stapler and first clamp jaw of the anvil, and cooperating ball and socket members on the second clamp jaw of the stapler and second clamp jaw of the anvil. The engagement structure can be adjustable to permit changes in the spacing between the first staple magazine and first anvil portion, and between the second staple magazine and the second anvil portion.

The anastomosis device can further include proximal engagement structure for engaging the stapler to the anvil. The engagement structure can include a latch on one of the stapler and the anvil, and a cooperating keeper on the other of the stapler and the anvil.

The lock for securing the clamp jaws of the stapler and the lock for securing the clamp jaws of the anvil in the clamping position can be of many different constructions. In one embodiment, the lock can comprise a ratchet.

The staple array can be any suitable array. The staple array can be a linear array. The staple array can include at least two rows.

There are shown in the drawings a linear anastomosis clamp and stapler device 100. The anastomosis device 100 includes a stapler 104 and an anvil 108. The stapler 104 and anvil 108 are separate pieces that are first used separately to initially clamp vessel ends, as retractors to hold vessel flaps apart, and then engaged and used together as an integrated device to perform anastomosis accurately and efficiently.

The stapler 104 includes a distal end 112 having jaws 120 and 124. The jaw 120 can communicate with a handle 128 and the jaw 124 can communicate with a handle 132. The anvil 108 include a distal end 116 having jaws 136 and 140. The jaw 136 can communicate with a handle 144 and the jaw 140 can communicate with a handle 148.

Figure 15:
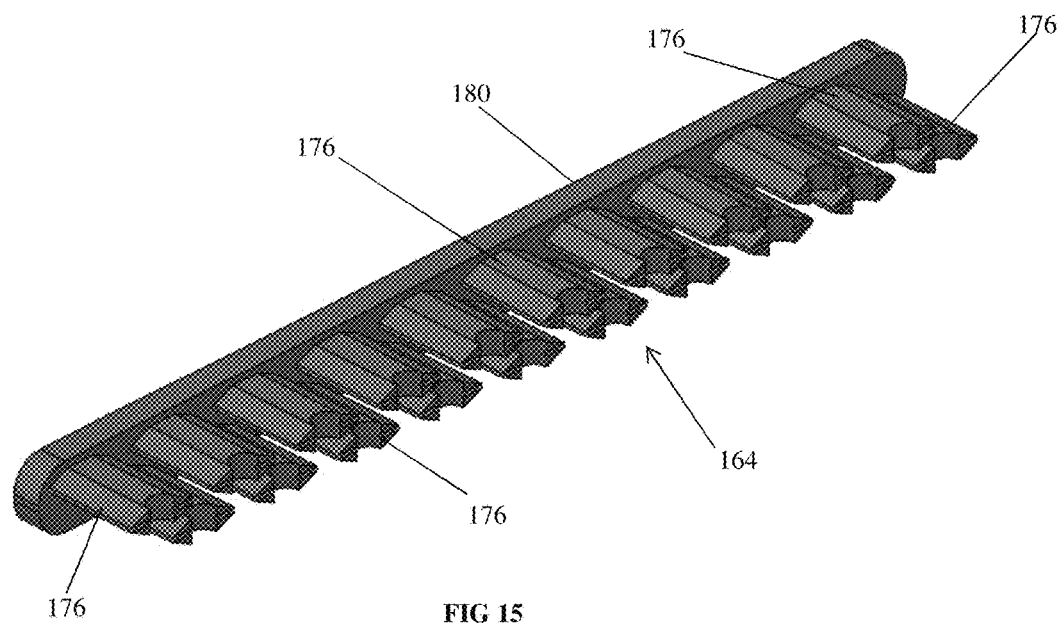
FIG. 15 is a perspective view of a staple piston.
Figure 16:
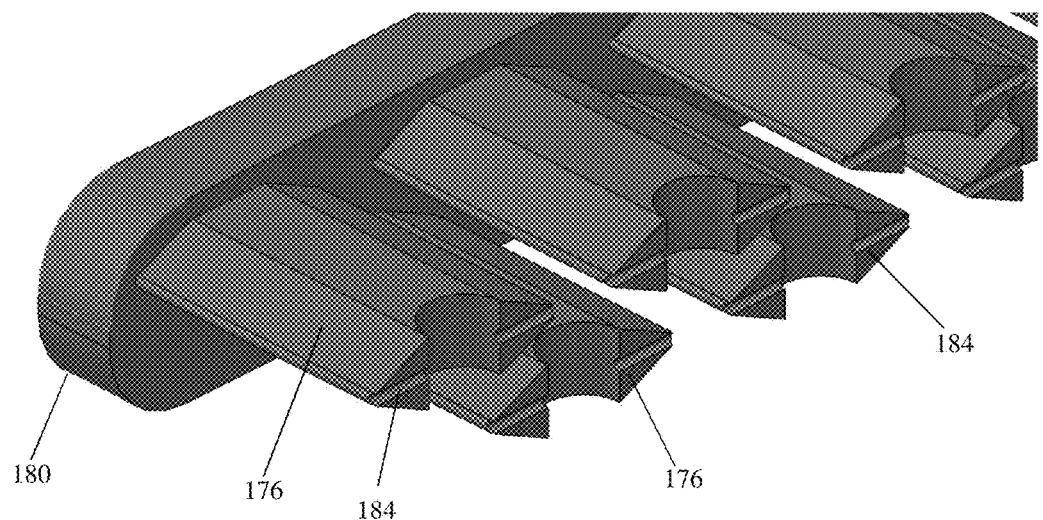
FIG. 16 is an enlarged perspective of a staple piston.

Each of the jaws 120 and 124 of the stapler 104 includes a staple magazine 156 for retaining an array of staples. As seen more particularly in FIGS. 8 and 9, the staple magazines 156 house staples 160 within staple bores 168. The staple piston 164 includes a plurality of staple seats 176 that are dimensioned to move within the staple bores 168 of the staple magazine 156. The staple magazines 156 can be formed integrally with the staple jaws 120 and 124, or formed separately from and detachable from the staple jaws 120 and 124. The staple seats 176 can have suitable structure such as staple grooves 184 for engaging the staples 160 (FIGS. 15-16). Movement of the staple seats 176 within the staple bores 168 will drive the staples 160 from the staple bores 168.

Figure 9:
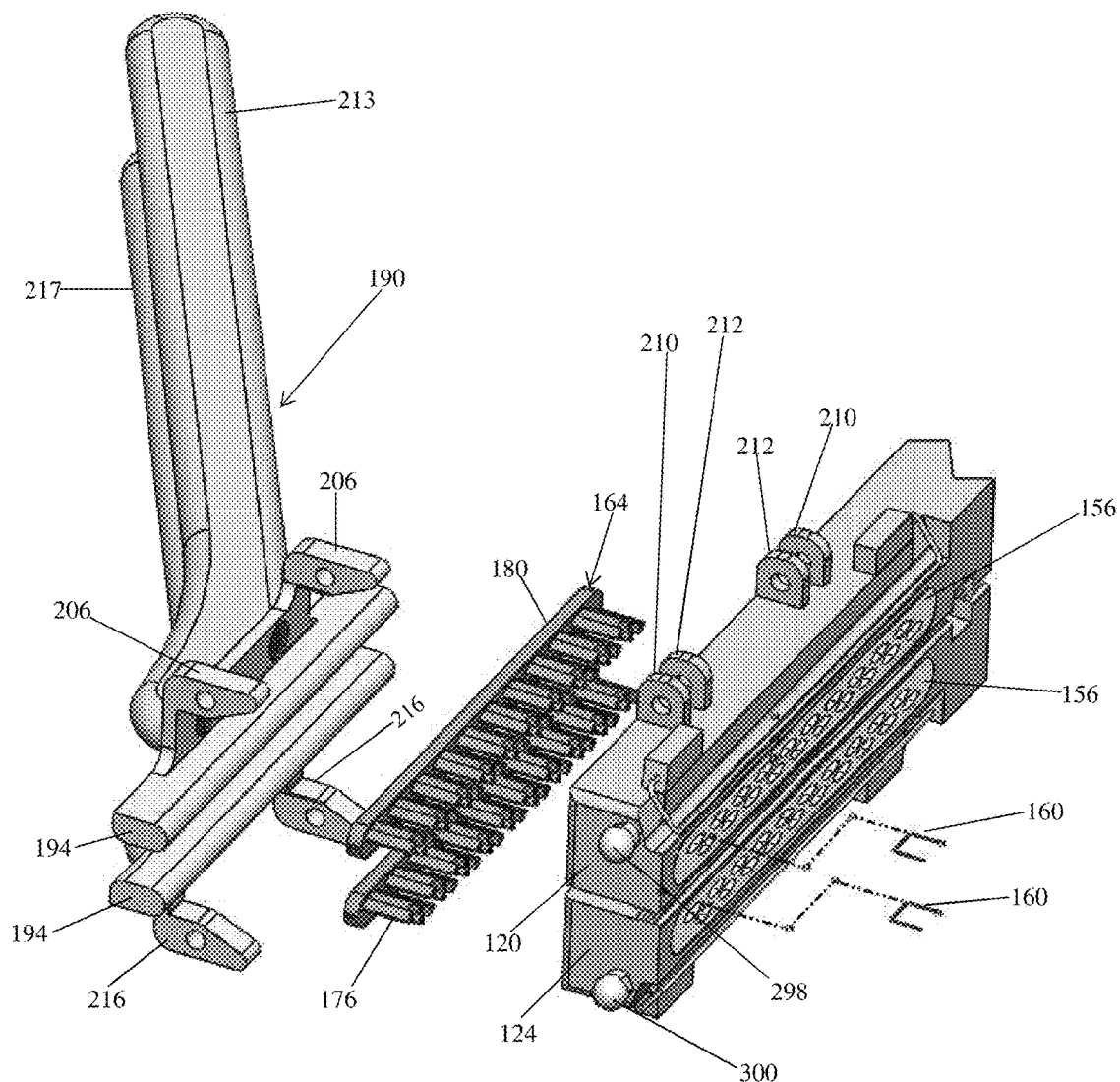
FIG. 9 is an exploded perspective view of staple jaws, staple magazines, staple plungers and operating levers, staple pistons and staples.
Figure 10:
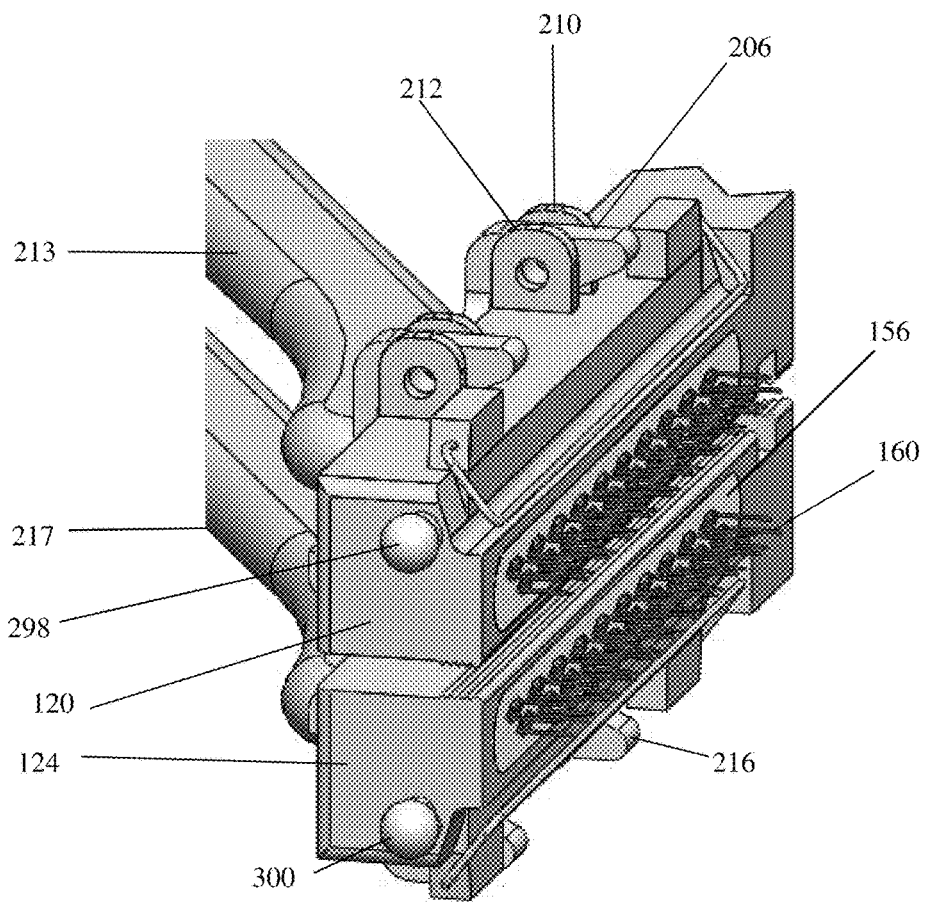
FIG. 10 is a front perspective view of staple jaws and staple magazines, in a staple-advanced mode of operation.
Figure 11:
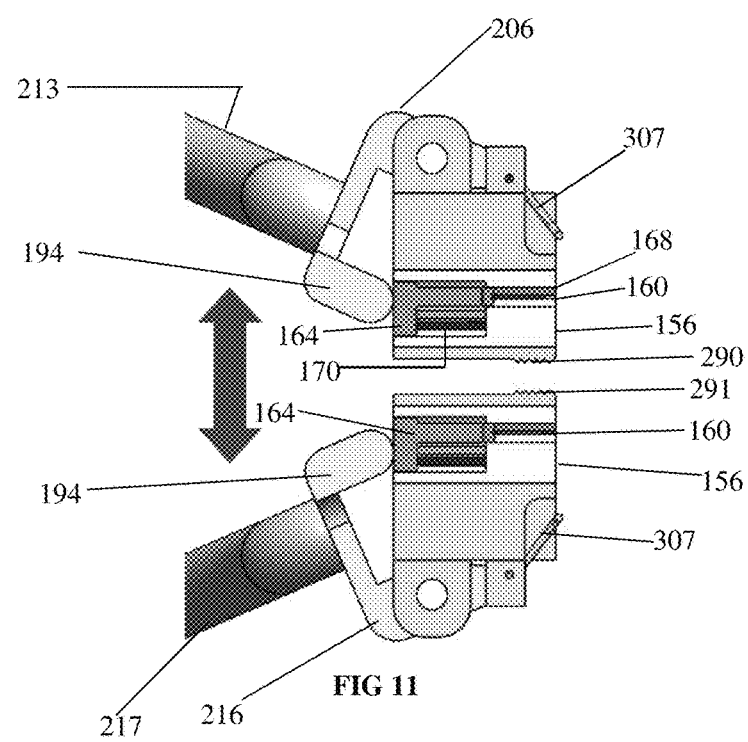
FIG. 11 is a cross-section of staple jaws, staple magazines, staple plungers and operating levers, staple pistons and staples, in a first mode of operation.
Figure 12:
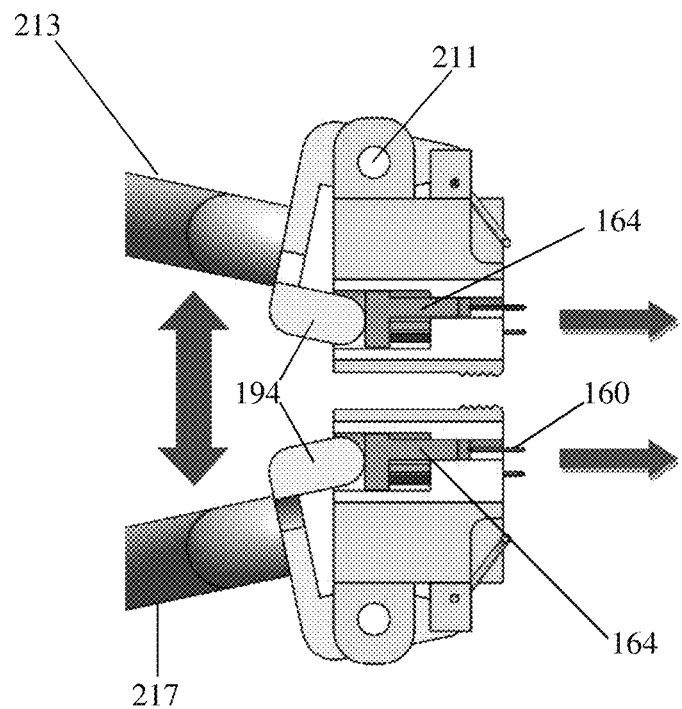
FIG. 12 is a cross-section in a second mode of operation.
Figure 13:
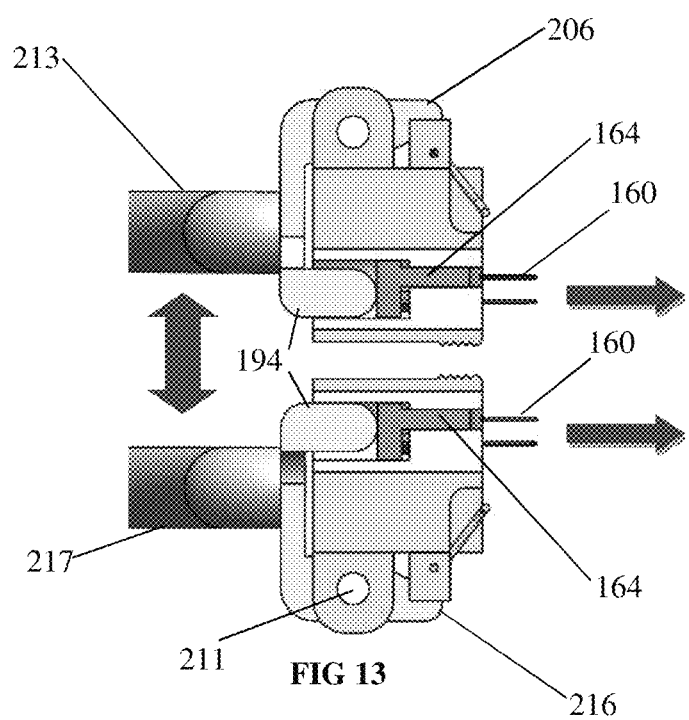
FIG. 13 is a cross-section in a third mode of operation.

Movement of the staple piston 164 can be accomplished by any suitable structure. In one embodiment, a driver 190 can include staple plungers 194 which contact a drive surface 180 of the staple pistons 164 (FIG. 9). The drive surface 180 of the staple piston 164 is moveable within a staple piston bore 170. A plunger 194 associated with jaw 120 can be connected by suitable structure such as upper hinge elements 206 that are secured between outer hinge seats 210 and inner hinge seats 212 and secured by pins 211 in apertures 228. Similarly a plunger 194 associated with jaw 124 can be connected by lower hinge elements 216 secured by between outer hinge seats 210 and inner hinge seats 212 by pins 211 in apertures 228. The plungers 194 can be connected to levers 213 and 217. Operation of the levers 213 and 217 causes the hinge elements 206 and 216 to be pivoted about pins 211, which will cause the drivers 194 to contact drive surfaces 180 of staple pistons 164. The staples 160 will thereby be driven from the staple bores 168 (FIGS. 10-13).

Figure 5:
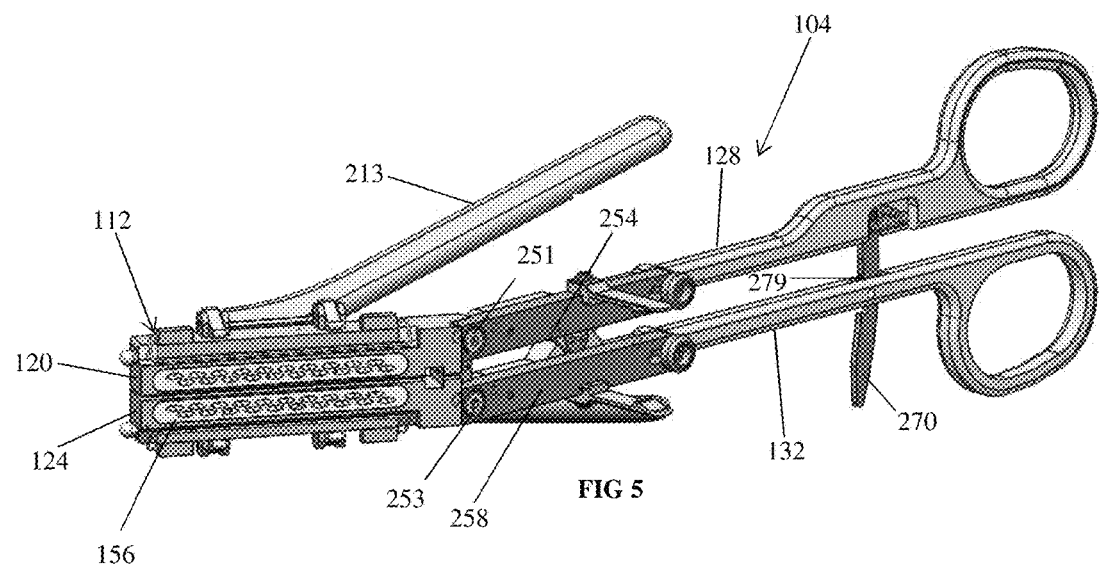
FIG. 5 is an inside perspective view of a stapler.
Figure 6:
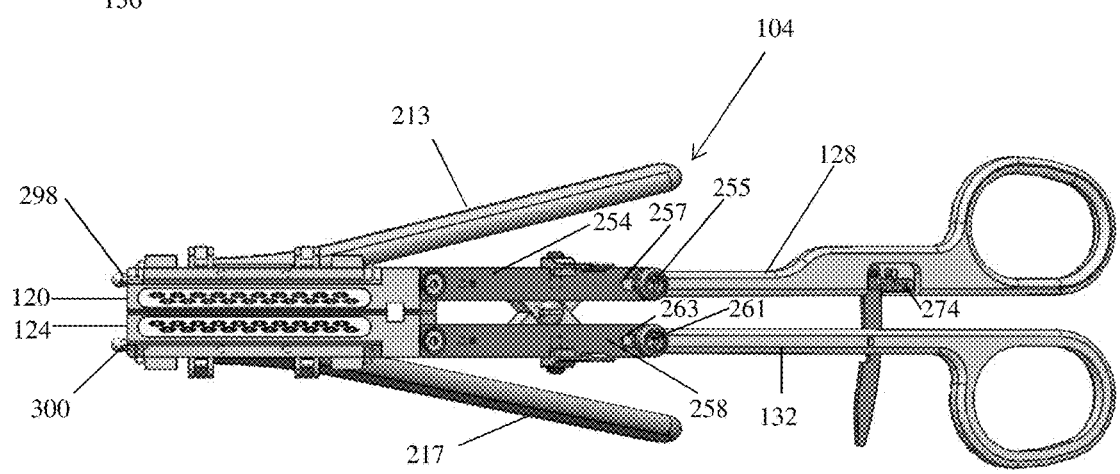
FIG. 6 is a side elevation of a stapler.
Figure 7:
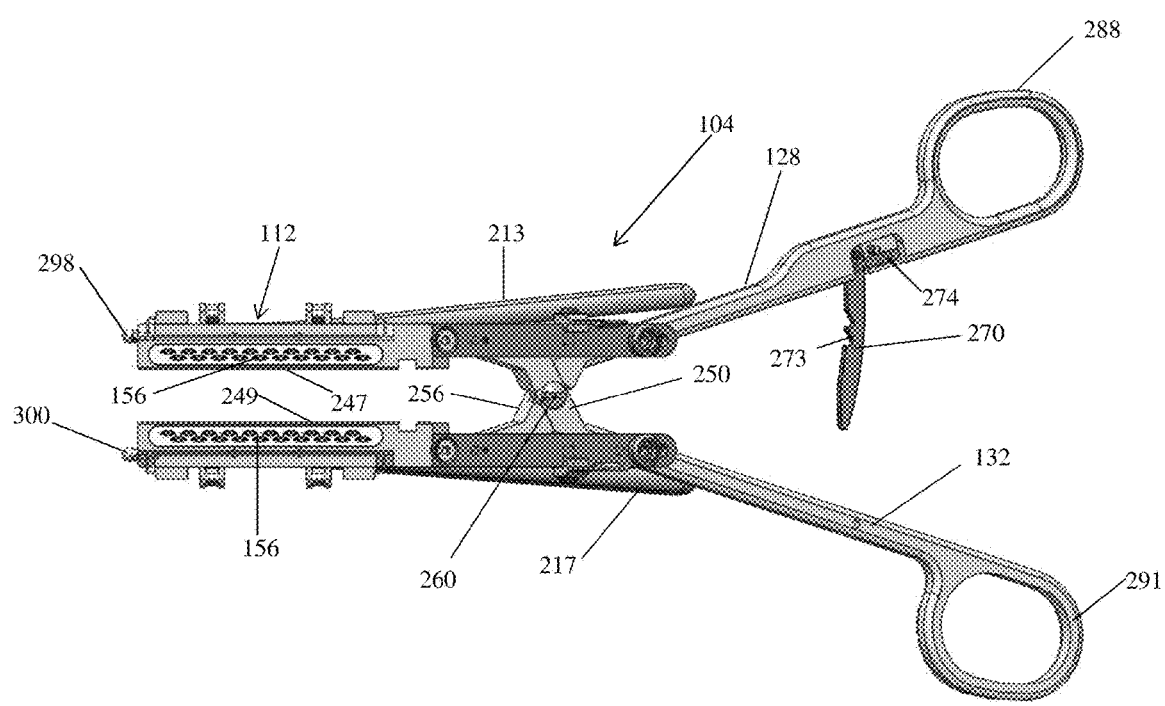
FIG. 7 is a side elevation of a stapler in an open configuration.

The stapler 104 is also capable of performing a clamping function, shown in FIGS. 5-7. Any suitable structure for the clamping function is possible. In one embodiment, the jaw 120 can have a clamping surface 247 and the jaw 124 can have a clamping surface 249. A jaw bracket 254 is connected to the jaw 120 and a jaw bracket 258 is connected to the jaw 124. Scissor elements 250 and 256 are pivotally connected by pin 260, and to the jaw brackets 254 and 258 about pivotal connections 251 and 253, and 255 and 261 (FIGS. 5-6). The pivotal connection 255 can be provided in a slot 257. The pivotal connection 261 can be provided in a slot 263.

Figure 14:
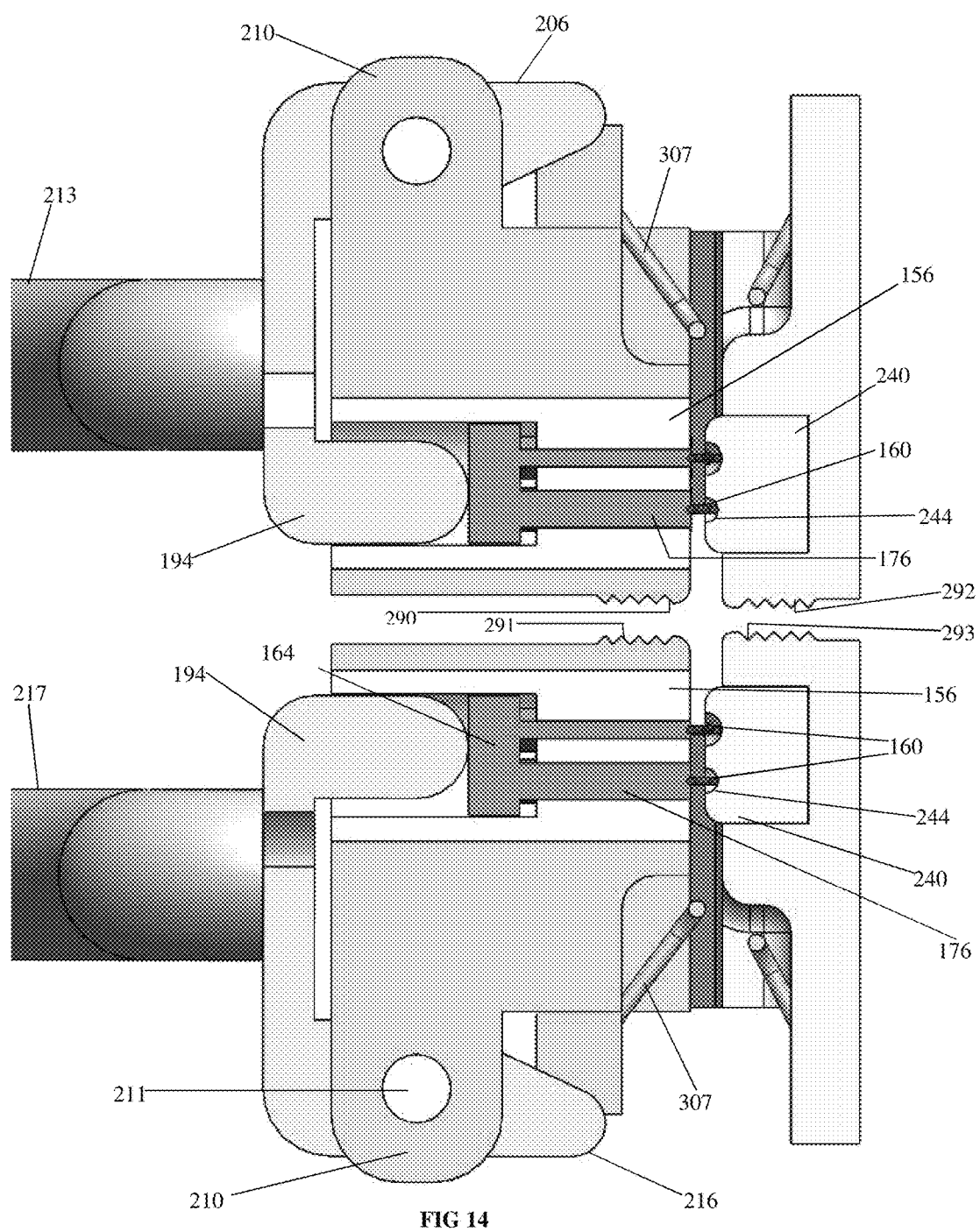
FIG. 14 is an enlarged cross-section in a third mode of operation, and including an anvil.

Manipulation of the handles 128 and 132 to the open position shown in FIG. 7 separates the jaws 120 and 124 and corresponding clamping surfaces 247 and 249 to an open configuration. Bringing the arms 128 and 132 together closes the jaws 120 and 124 as shown in FIGS. 5-6. This can be used to clamp vessels during the anastomosis procedure. Gripping surface such as teeth 290 and 291 can be provided on the clamping surfaces 247 and 249 to prevent slippage of the clamped vessel (FIG. 14). The handles 128 and 132 can have finger grip loops 288 and 291. A lock can be provided to retain the clamping position such that constant clamping force by the user is not necessary. Different locking mechanisms are possible. There is shown a ratchet arm 270 which can be actuated by spring 274 and includes teeth 273 to engage corresponding structure in opening 279 of arm 132 to lock the arms 128 and 132 together in the clamping position (FIGS. 5-7). Physical manipulation by the user against the action of the spring 274 removes the teeth 273 from engagement and releases the handles 128 and 132 to the open position shown in FIG. 7.

Figure 19:
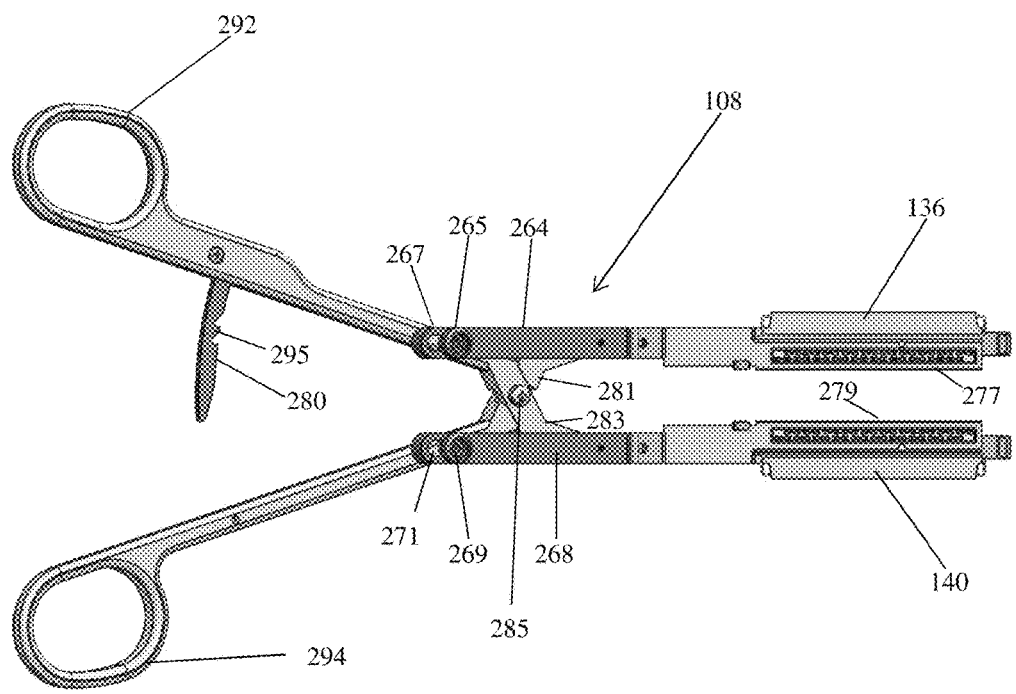
FIG. 19 is an inside elevation of an anvil, in an open configuration.

The anvil 108 is also capable of performing a clamping function, as shown in FIGS. 19-22. The jaw 136 can have a clamping surface 277 and the jaw 140 can have a clamping surface 279 (FIG. 19). A jaw bracket 264 is connected to jaw 136, and a jaw bracket 268 is connected to jaw 140. Scissor elements 281 and 283 are pivotally connected by pin 285 and to the jaw brackets 264 and 268 about pivotal connections 265 and 269 and 289 and 291. The pivotal connection 265 can be provided in a slot 267. The pivotal connection 269 can be provided in a slot 271. The handles 144 and 148 can have finger grip loops 292 and 294 manipulation of the device.

Figure 20:
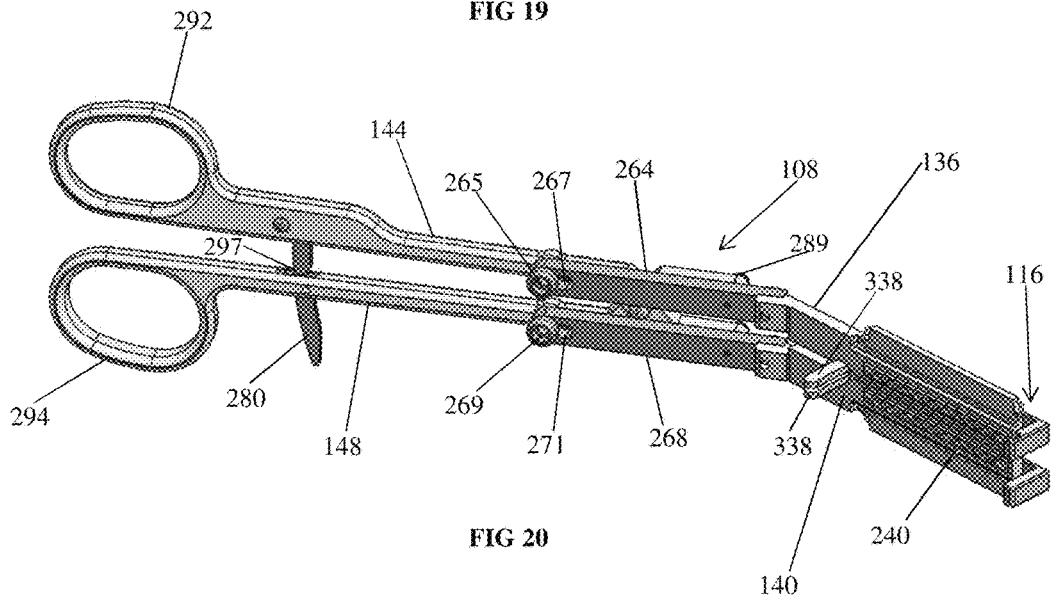
FIG. 20 is an inside perspective view of an anvil, in a clamping configuration.
Figure 21:
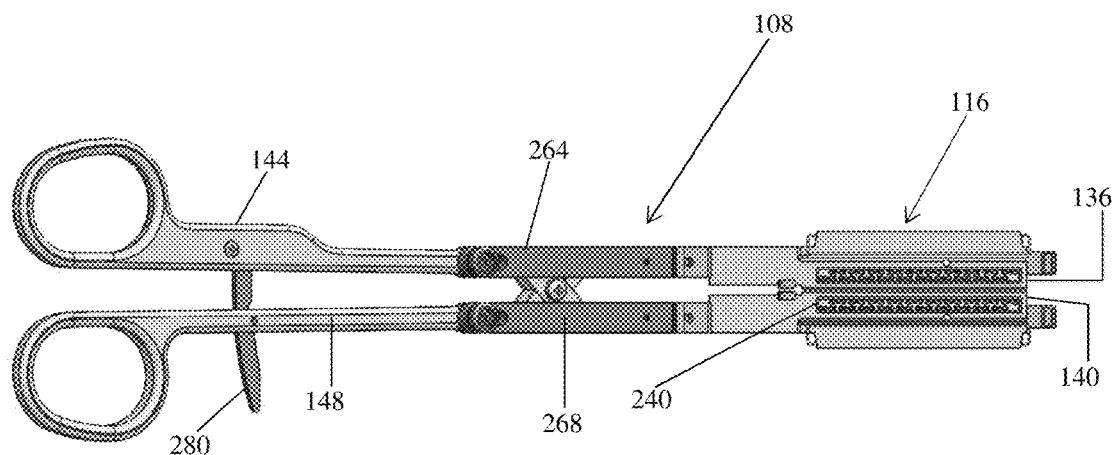
FIG. 21 is an inside elevation of an anvil, in a clamping configuration.

Manipulation of the handles 144 and 148 to the open position shown in FIG. 19 separates the jaws 136 and 140 and corresponding clamping surfaces 277 and 279 to an open configuration. Bringing the handles 144 and 148 together closes the jaws 136 and 140 as shown in FIGS. 20-21. This can be used to clamp vessels during the anastomosis procedure. Gripping surfaces 292 and 293 can be provided to prevent slippage of the clamped vessel (FIG. 14). A lock can be provided to retain the clamping position such that constant clamping force by the user is not necessary. Different locking mechanisms are possible. There is shown a ratchet arm 280 which can be actuated by a spring (not shown) and includes teeth 295 to engage corresponding structure in opening 297 of arm 148 to lock the handles 144 and 148 together in the clamping position (FIGS. 20-21). Physical manipulation by the user against the action of the spring removes the teeth 295 from engagement and releases the handles 144 and 148 to the open position shown in FIG. 19.

Figure 17:
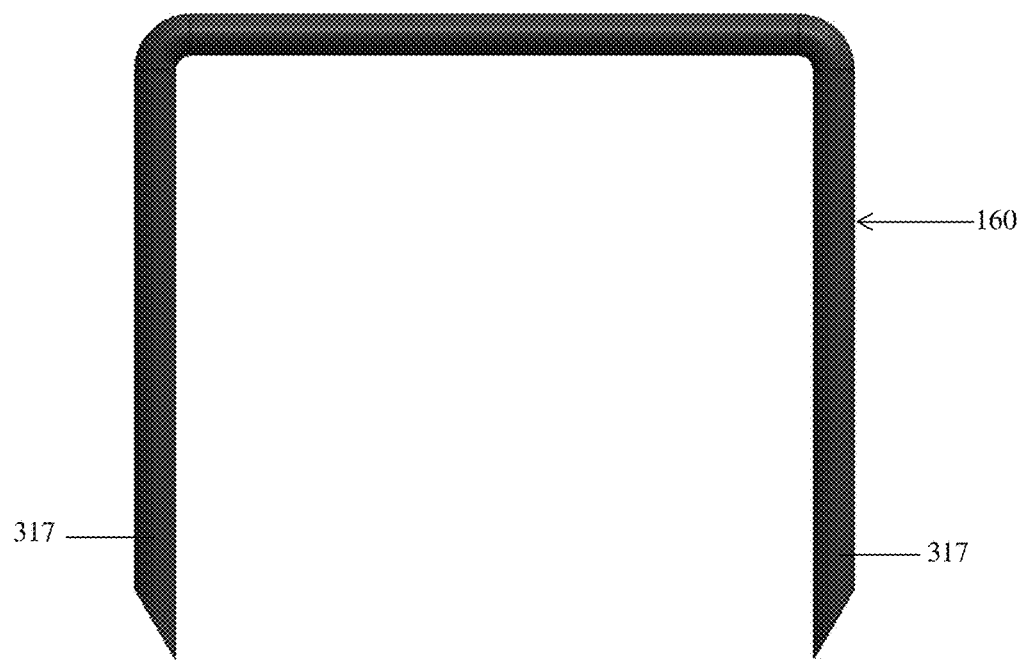
FIG. 17 is a plan view of a staple, in a first mode of operation.
Figure 18:
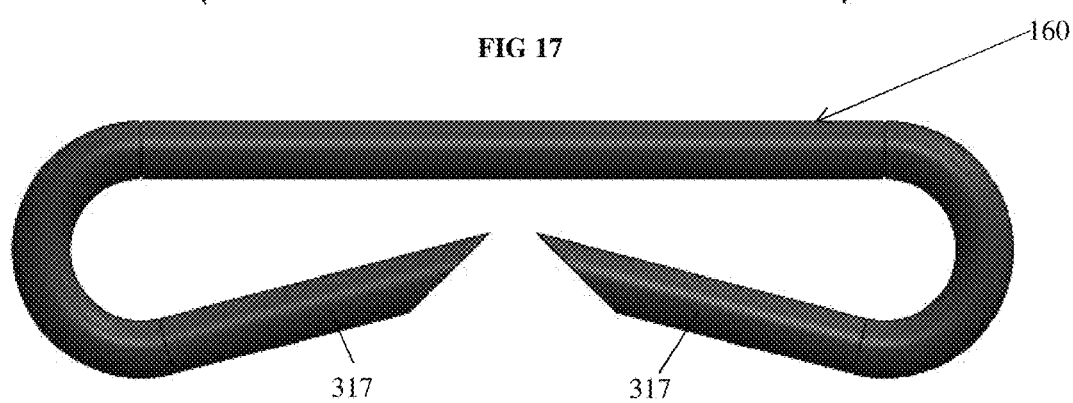
FIG. 18 is a plan view of a staple, in a second mode of operation.

The anvil 108 can includes a plurality of individual anvil surfaces 244 for closing the staples 160 when the staples are driven against the anvil surfaces 244. The anvil surfaces 244 can be provided in an insert 240 or formed integrally with the jaws 136 and 140. The staples 160 are shown in FIGS. 17-18. Any suitable staples are possible. The ends 317 of the staples 160 are driven inward or outward and rearward as shown in FIG. 18 by the contour of the anvil surfaces 244 as is known in the stapling art. Different staple and anvil designs are possible.

Figure 22:
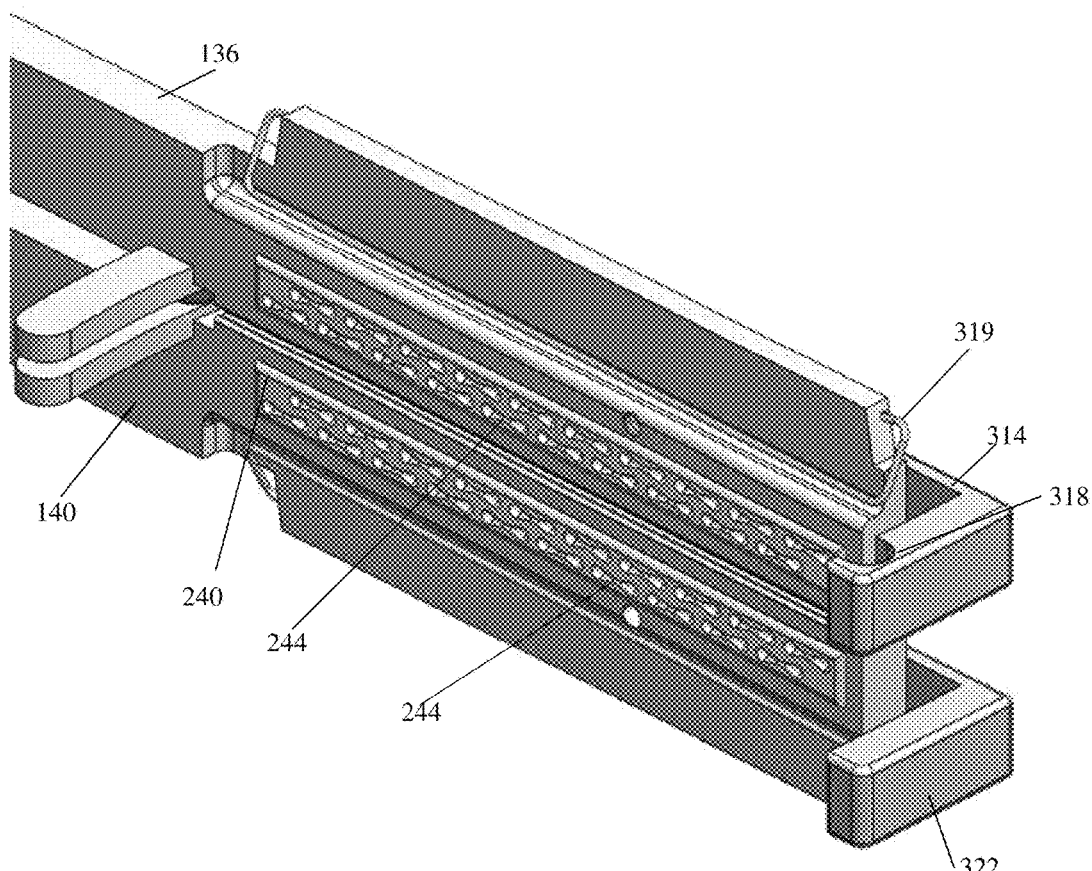
FIG. 22 is an enlarged perspective of anvil jaws and anvil portions, in a clamping configuration.

The stapler 104 and anvil 108 can be used separately as clamps and as a single combined device 100 for the anastomosis procedure. A detachable engagement structure is provided to secure the stapler 104 to the anvil 108 for the stapling procedure. Any suitable engagement structure can be utilized. The engagement structure can be distal, proximal or intermediate. There is shown in the figures distal engagement structure comprising a ball and socket construction. In this embodiment, balls 298 and 300 are provided on the jaw member 120 and 124, respectively (FIG. 9). Corresponding sockets 318 can be provided on a socket arm 314 provided on jaw 136 of anvil 108, and on a socket arm 322 connected to jaw 140 (FIG. 22). The socket arms 314 and 322 can be in the form of leaf springs to provide some flexibility in the engagement. This will allow greater spacing between the stapler 104 and anvil 108 where thicker vessels are to be joined.

Figure 8:
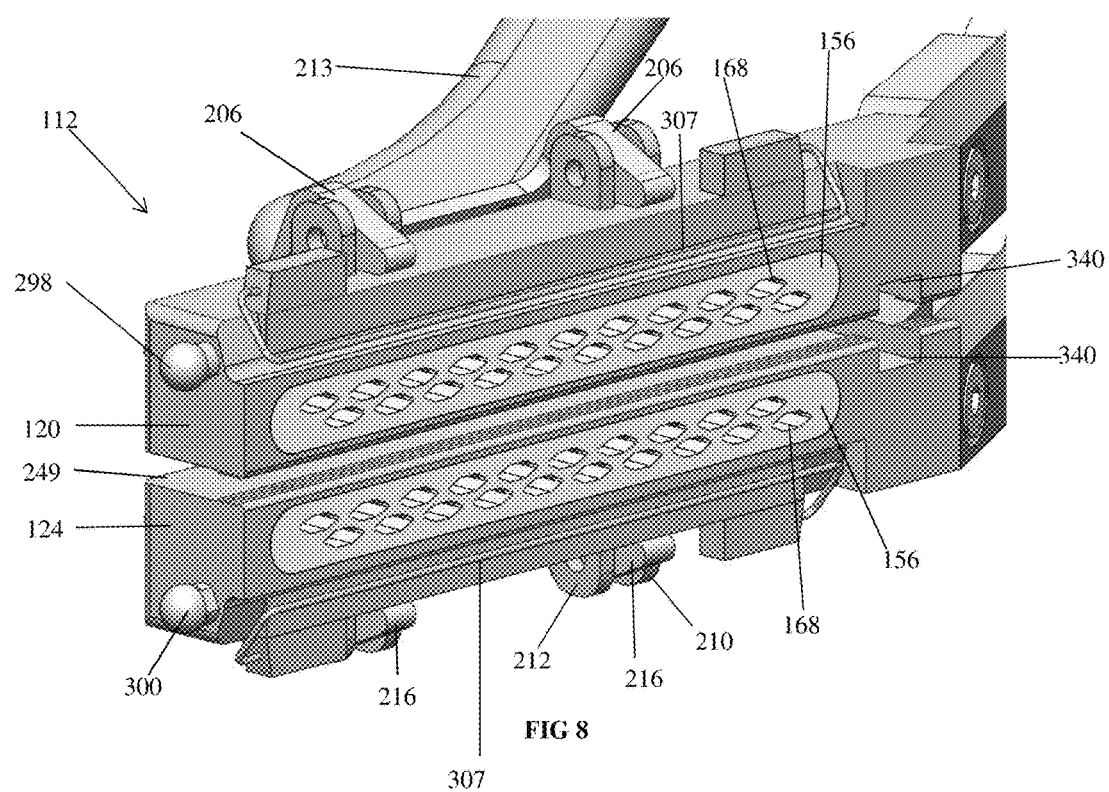
FIG. 8 is an enlarged perspective view of staple jaws and staple magazines.

Alternative or additional engagement structure is also possible. Catches 330 can be provided on the stapler 104 with inclined catch surfaces 334 to engage corresponding structure on the anvil 108. Also, alignment arms 338 can be provided on the anvil 108 (FIG. 20), and can be received in corresponding openings 340 in the jaws 120 and 124 of the stapler 104 (FIG. 8). In addition to an engagement function, this will ensure proper alignment and registration of the staples 160 with the anvil surfaces 244. In this manner, all staples 160 in the array will be properly closed when the anastomosis is performed.

Figure 23:
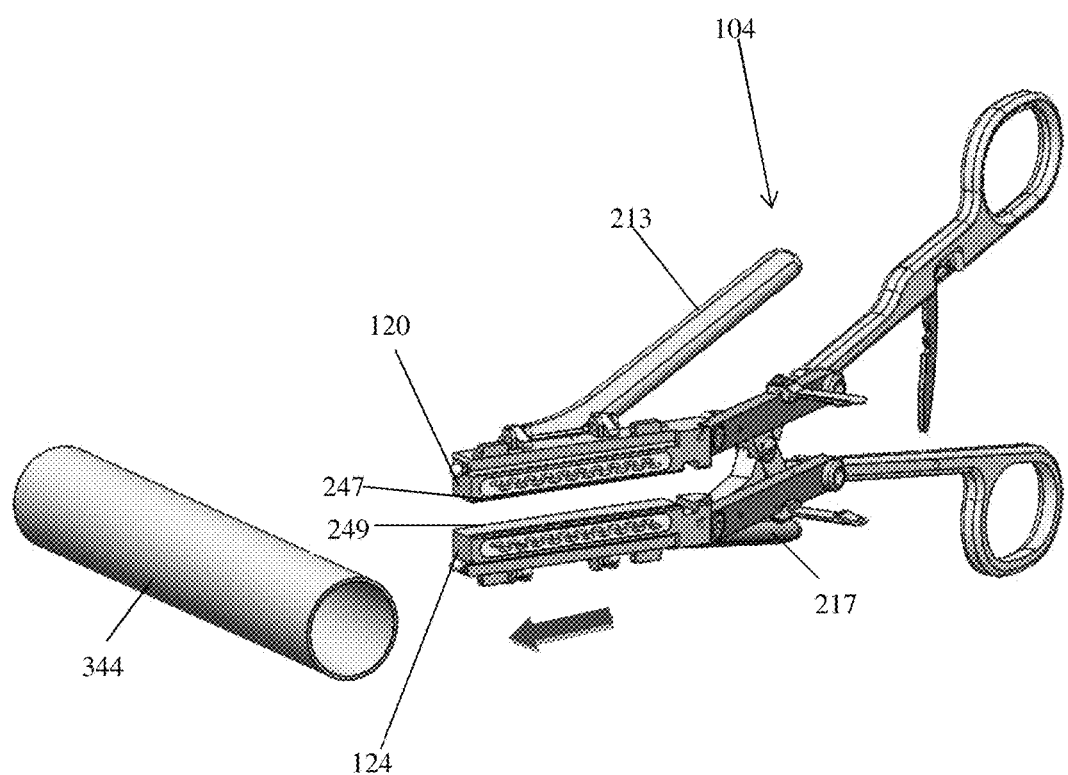
FIG. 23 is a perspective view of a stapler and a vessel in an initial mode of operation.
Figure 24:
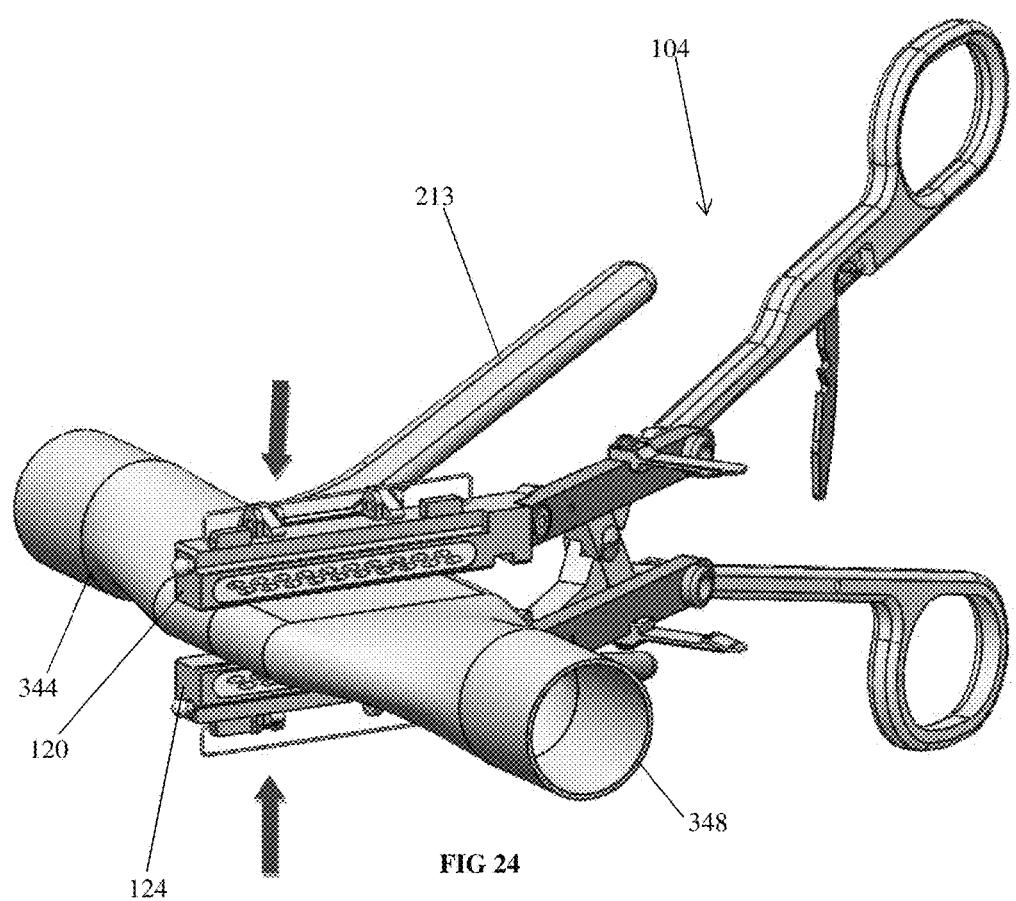
FIG. 24 is a perspective view in a second mode of operation.
Figure 25:
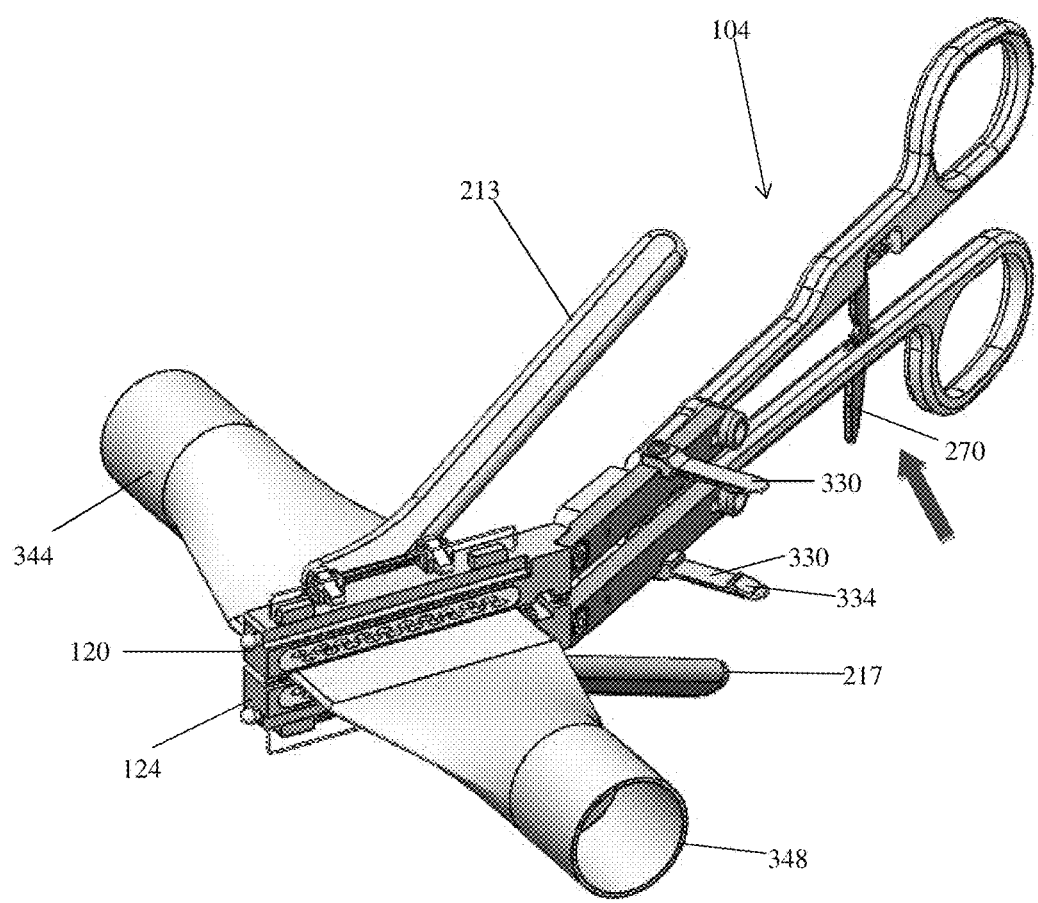
FIG. 25 is a perspective view in a third mode of operation.
Figure 26:
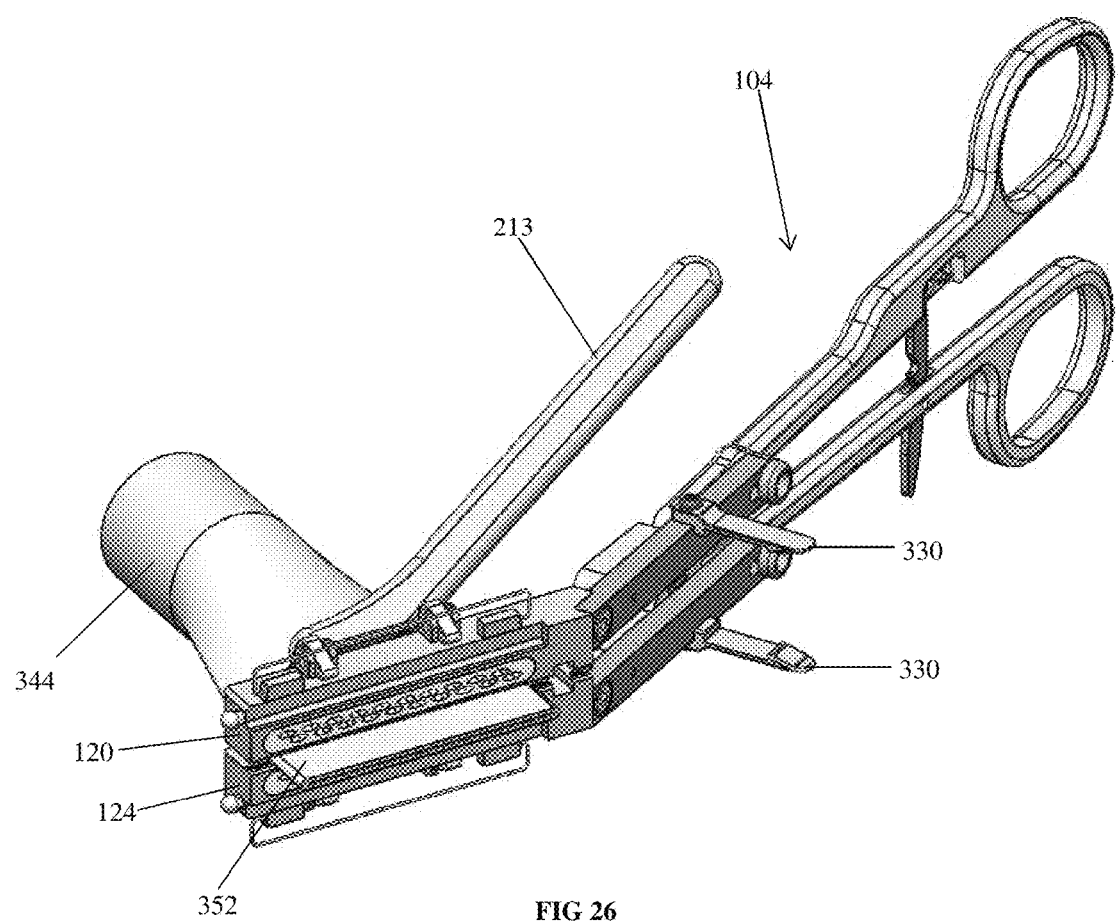
FIG. 26 is a perspective view in a fourth mode of operation.
Figure 27:
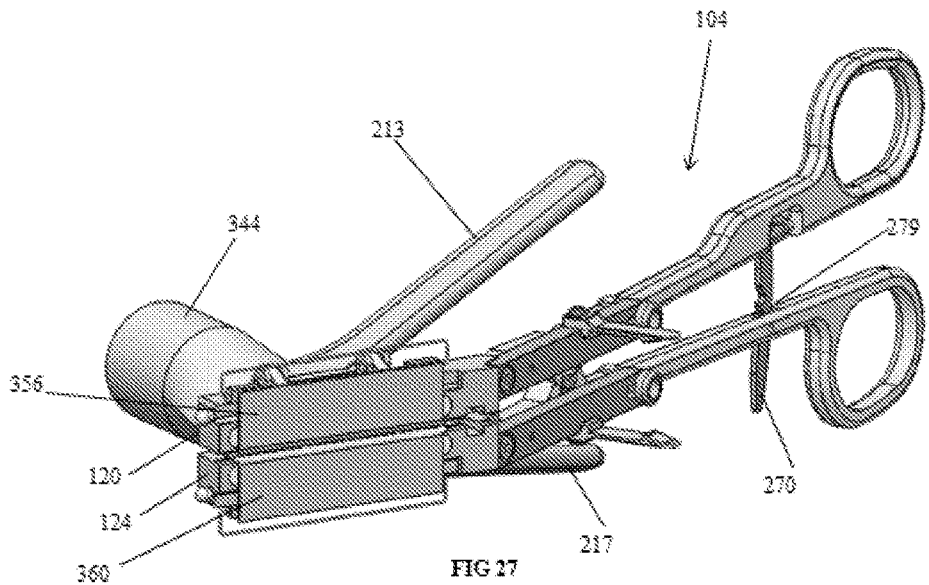
FIG. 27 is a perspective view in a fifth mode of operation.
Figure 28:
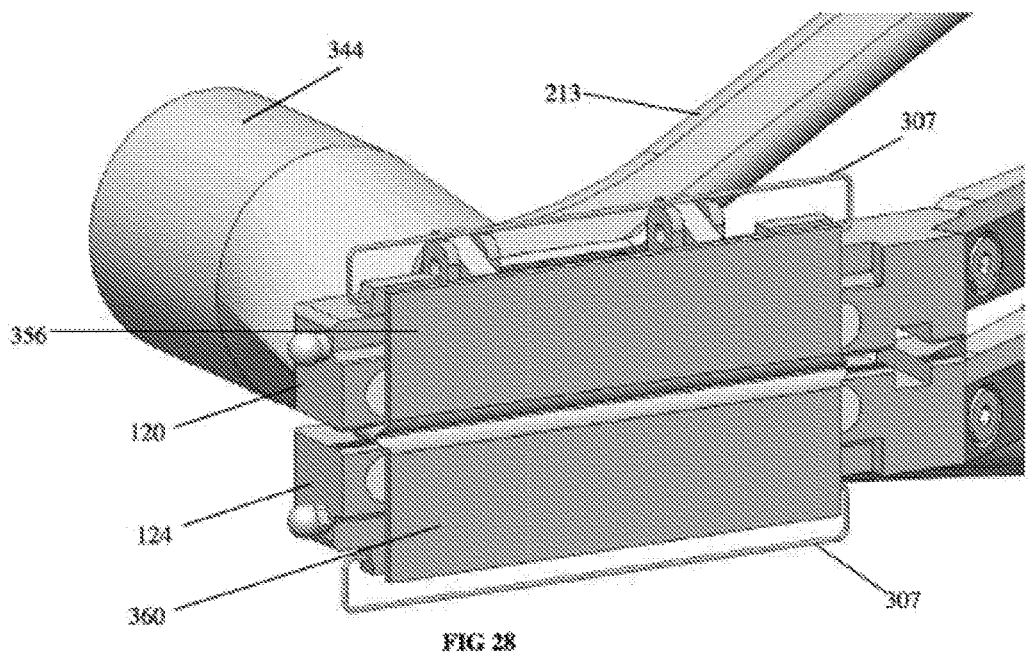
FIG. 28 is an enlarged perspective of staple jaws in the fifth mode of operation.
Figure 29:
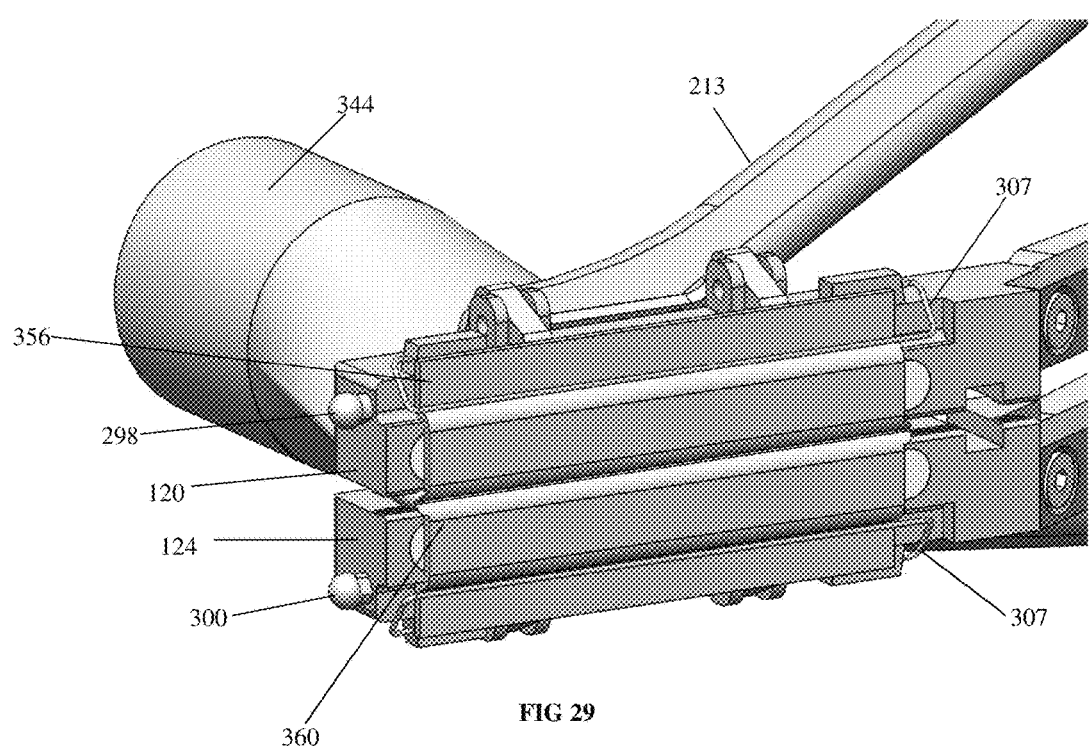
FIG. 29 is an enlarged perspective of staple jaws in a sixth mode of operation.

A method of performing anastomosis with the linear anastomosis clamp and stapler 100 of the invention is depicted in FIGS. 23-49. A clamping function is performed first with either or both of the stapler 104 and anvil 108 in any order of application. There is shown in FIG. 23 a stapler 104 being positioned over a vessel 344 with the jaws 120 and 124 in the open position. When the jaws 120 and 124 our positioned over the vessel 344, the handles 128 and 132 are brought together as shown in FIG. 24 and the jaws 120 and 124 will close in the direction of the arrows. The lock 270 will engage to retain the jaws 120 and 124 of the stapler 104 in the clamping position, as indicated by the arrow in FIG. 25. The end 348 of the vessel 344 can then be cut leaving a clamped end 352 (FIG. 26). It will be appreciated that the invention can be utilized on a vessel that has already been cut, in which case the clamp of the stapler 104 would replace or be in addition to an existing clamp on the vessel. The end 352 is cut at the edges to form flaps 356 and 360 (FIG. 27-28). Structure can be provided to retain the flaps. Spring arms 307 can be rotated into position to retain the flaps 356 and 360 (FIG. 29). Other flap retaining structure is possible.

Figure 30:
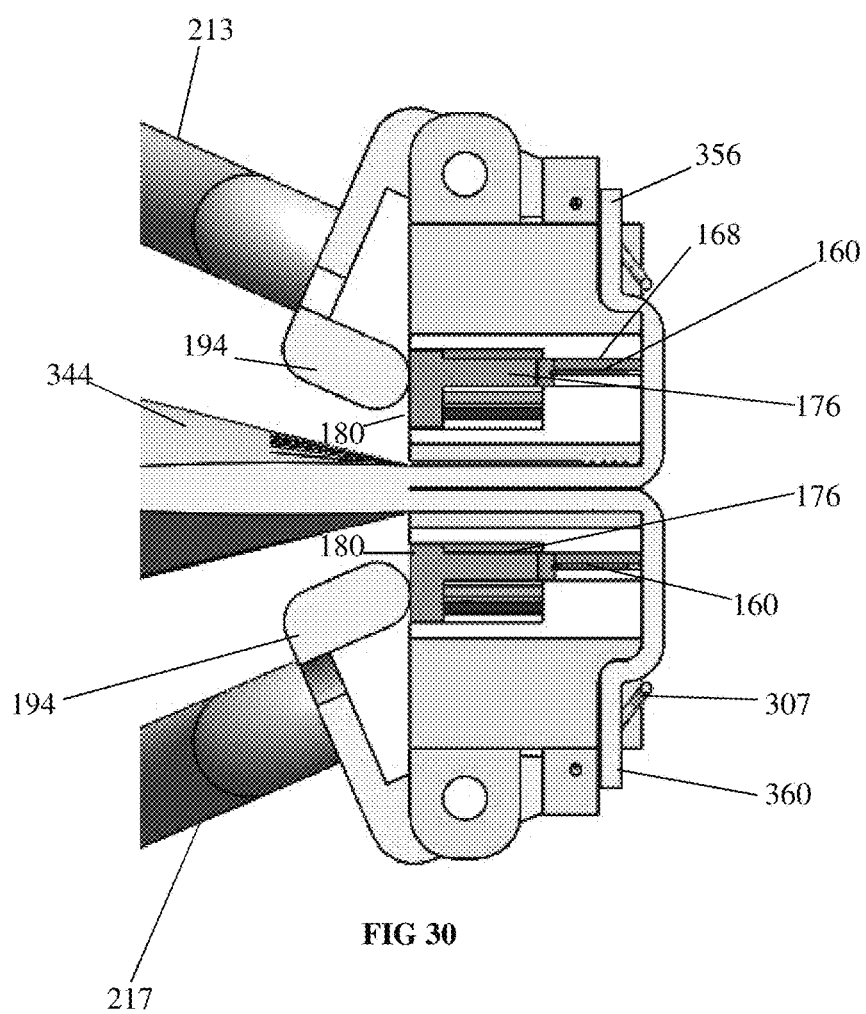
FIG. 30 is a cross-section of a vessel staple jaws, staple plungers, staple pistons, staples and tissue flaps in an initial mode of operation.
Figure 31:
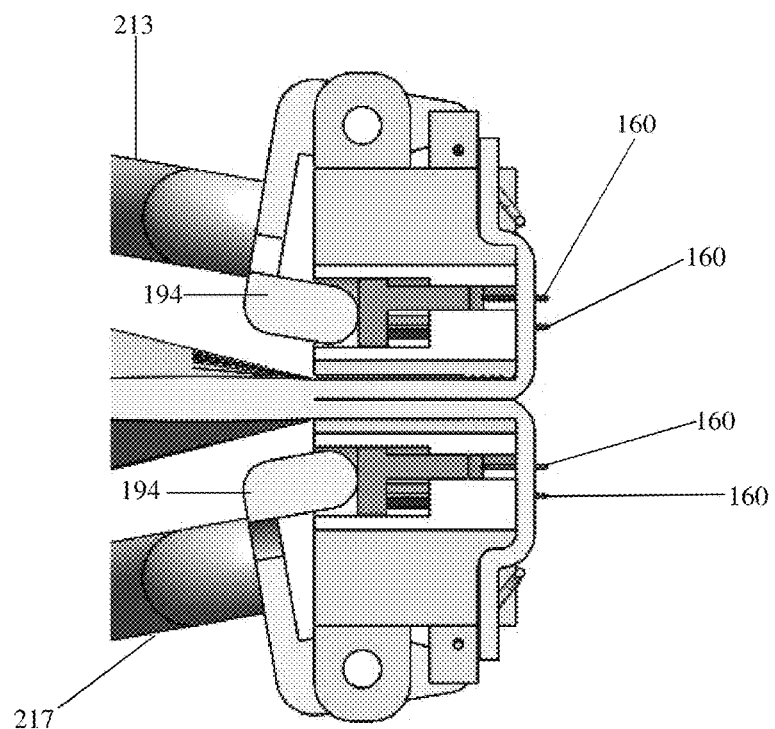
FIG. 31 is a cross-section in a staple-advanced mode of operation.

The levers 213 and 217 will initially be in the open, initialized position with the staples 160 within the staple bores 168 (FIG. 30). Movement of the levers 213 and 217 will cause the staple drivers 194 to contact the staple pistons 164 and drive the staples 160 through the flaps 356 and 360 as shown FIG. 31 without the anvil 108 for purposes of illustration. The anvil 108 must first be positioned adjacent the stapler 104 prior to commencing the stapling procedure.

Figure 32:
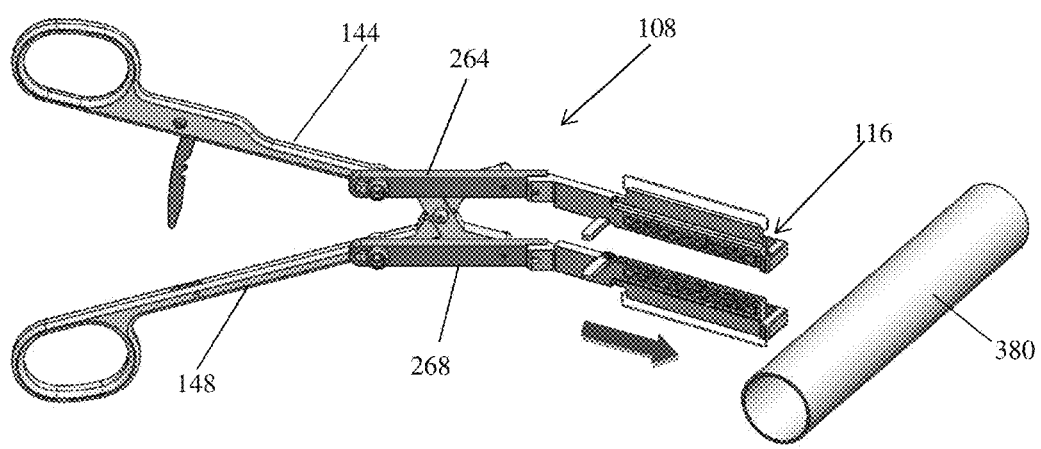
FIG. 32 is a perspective view of an anvil and vessel in a first mode of operation.
Figure 33:
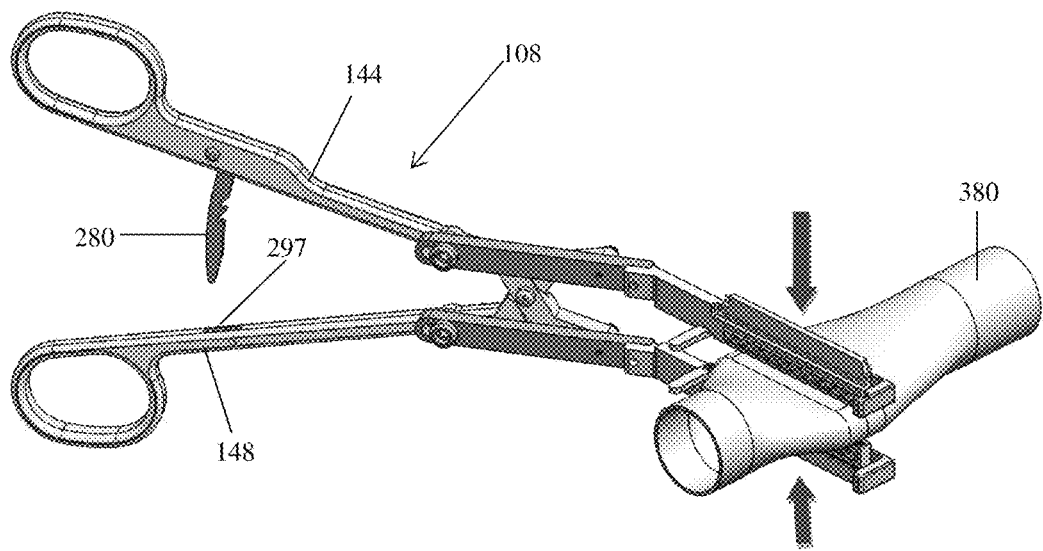
FIG. 33 is a perspective view of an anvil and vessel in a second mode of operation.
Figure 34:
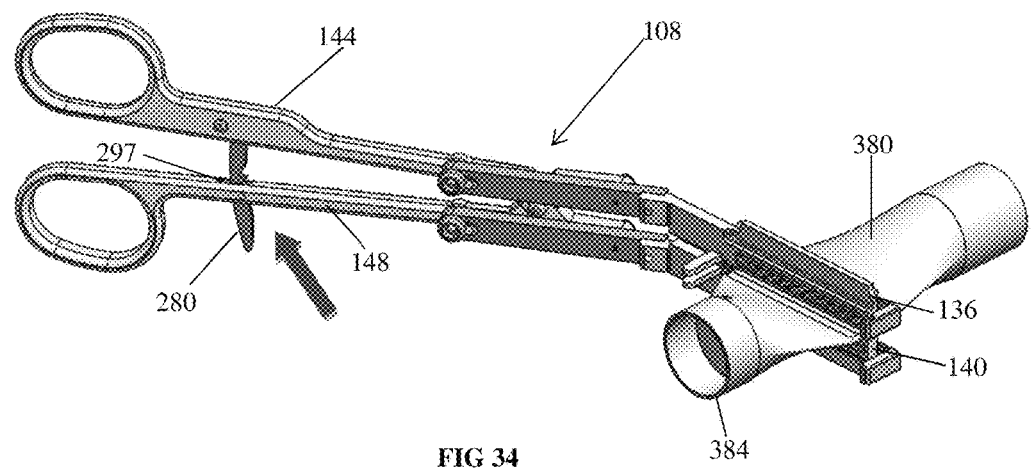
FIG. 34 is a perspective view of an anvil and vessel in a third mode of operation.
Figure 35:
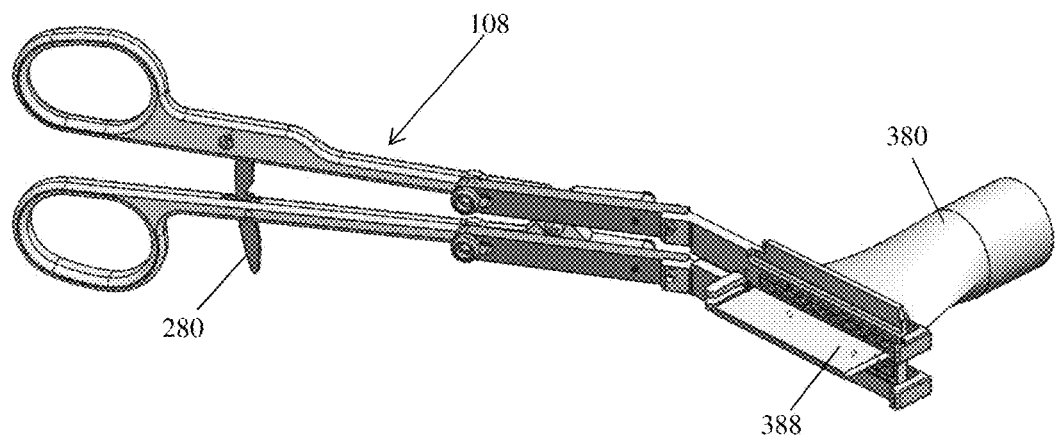
FIG. 35 is a perspective view of an anvil and vessel in a fourth mode of operation.
Figure 36:
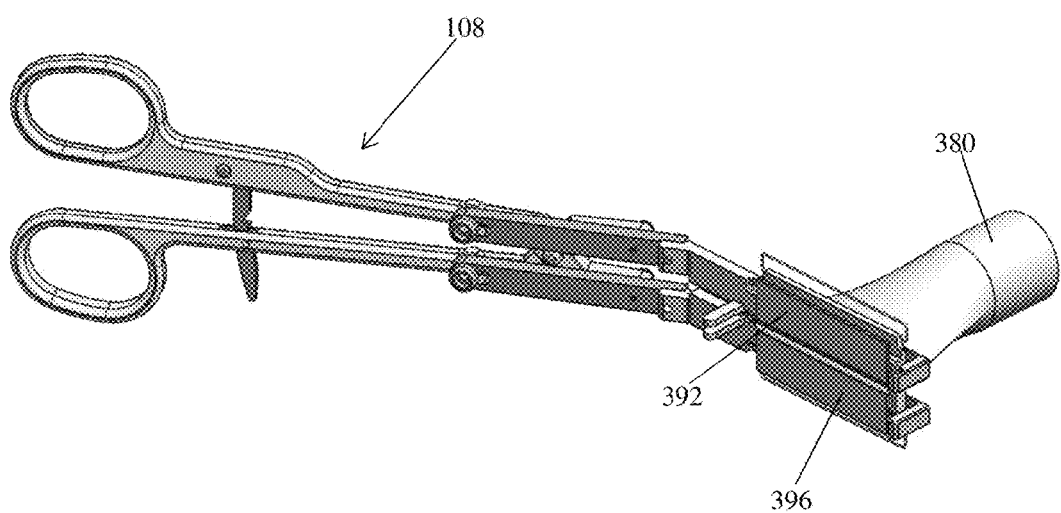
FIG. 36 is a perspective view of an anvil and vessel in a fifth mode of operation.
Figure 37:
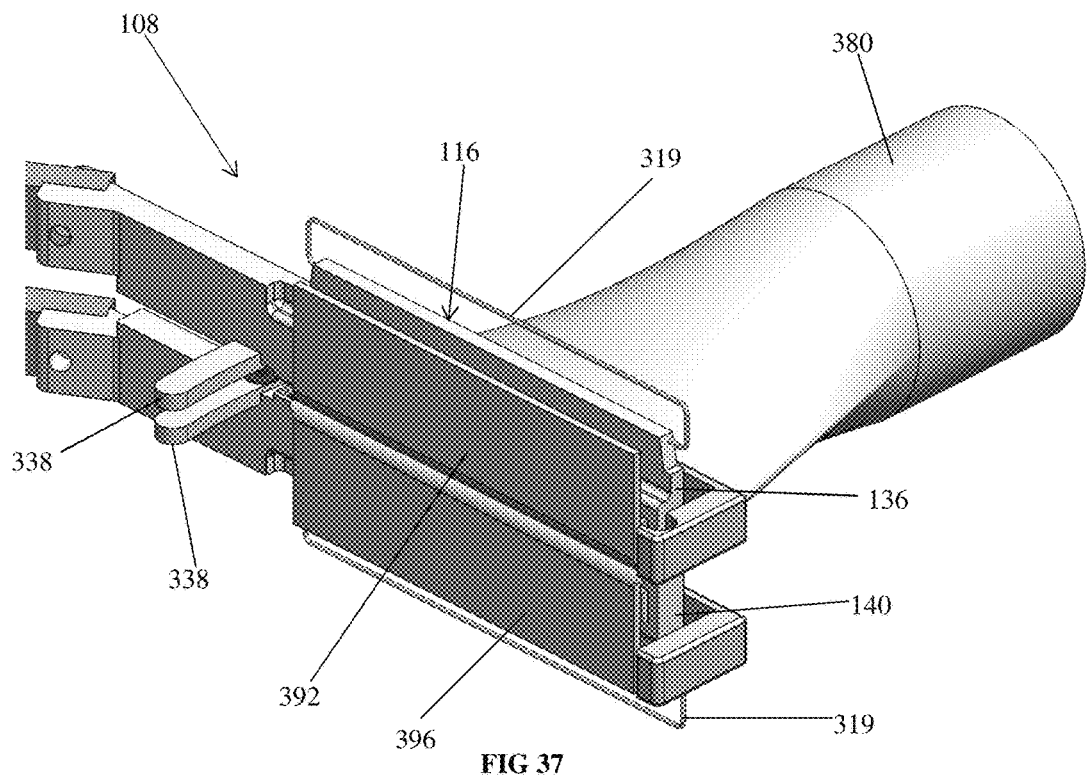
FIG. 37 is an enlarged perspective view of anvil jaws and the vessel in the fifth mode of operation.
Figure 38:
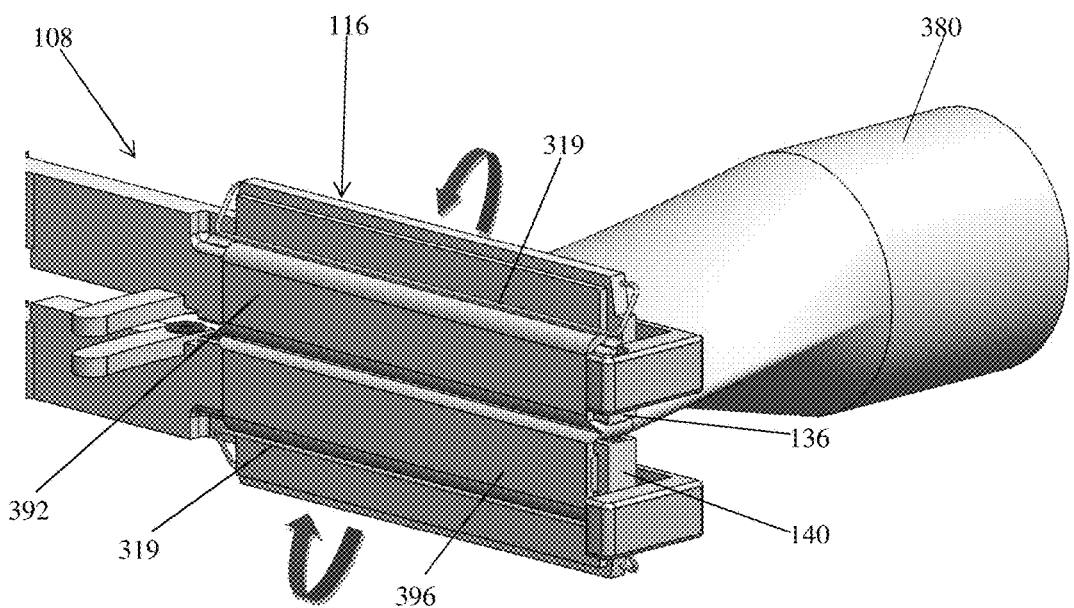
FIG. 38 is an enlarged perspective view of anvil jaws and the vessel in a sixth mode of operation.
Figure 39:
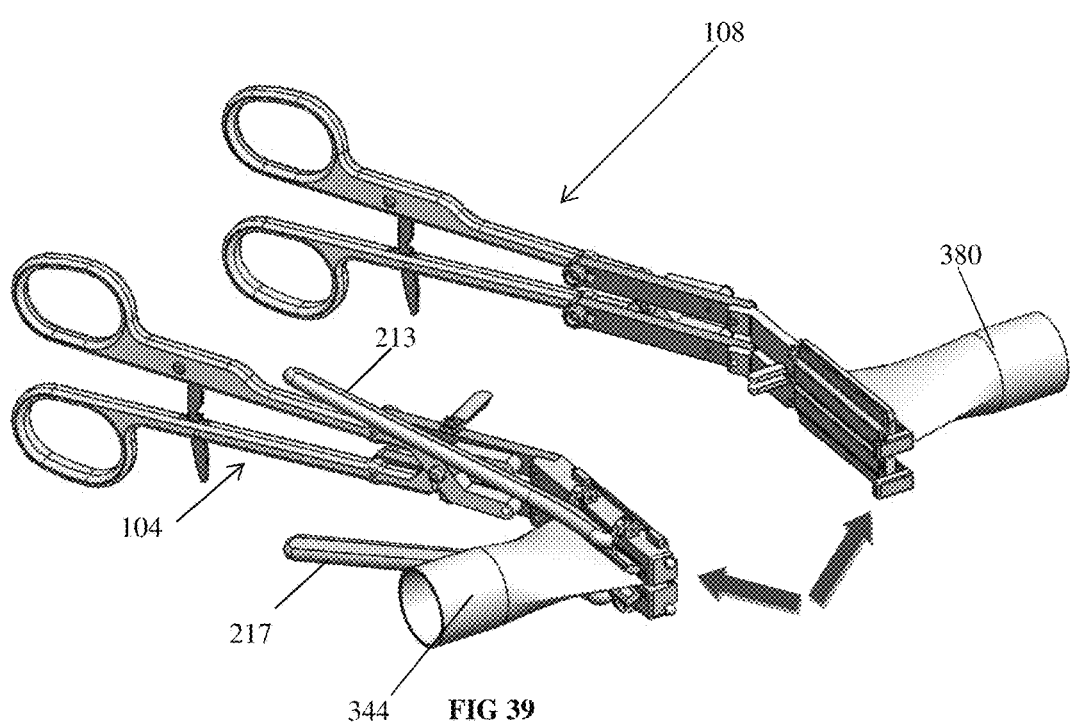
FIG. 39 is a perspective view of a stapler and an anvil in a first anastomosis configuration
Figure 40:
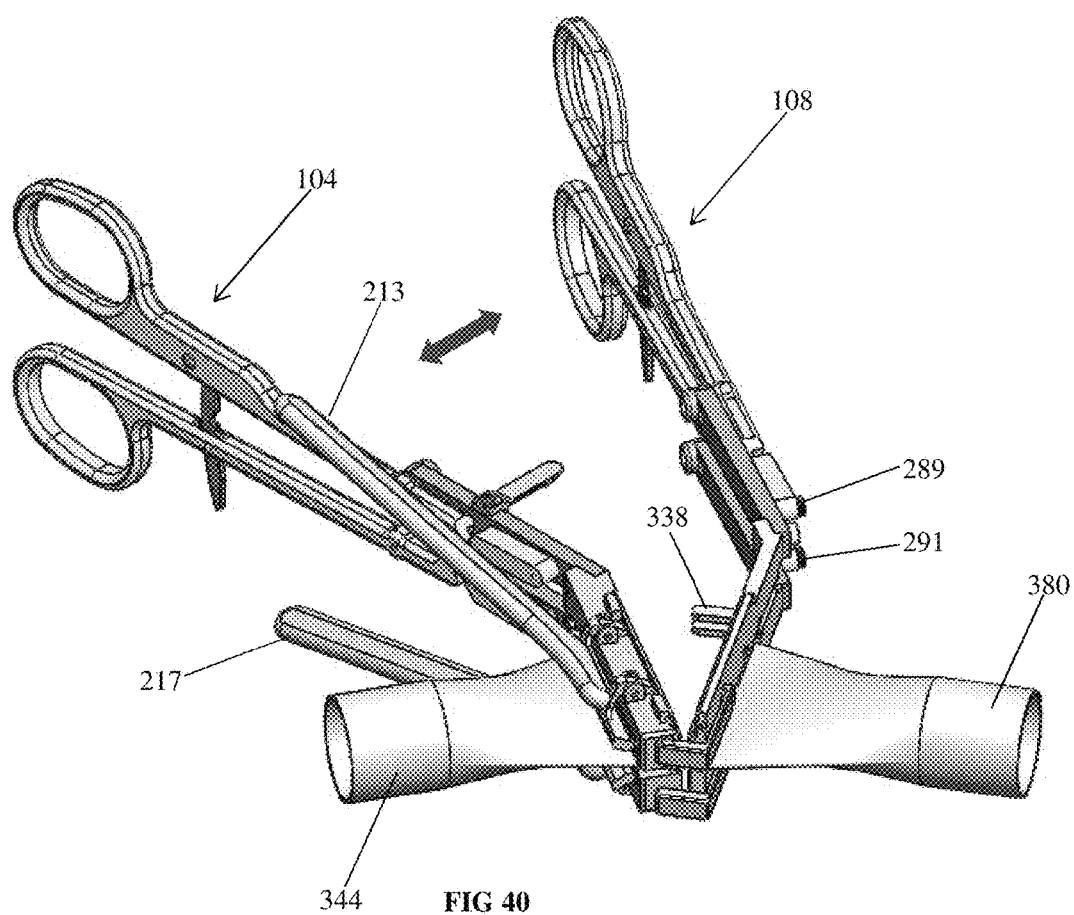
FIG. 40 is a perspective view of a stapler and an anvil in a second anastomosis configuration.
Figure 41:
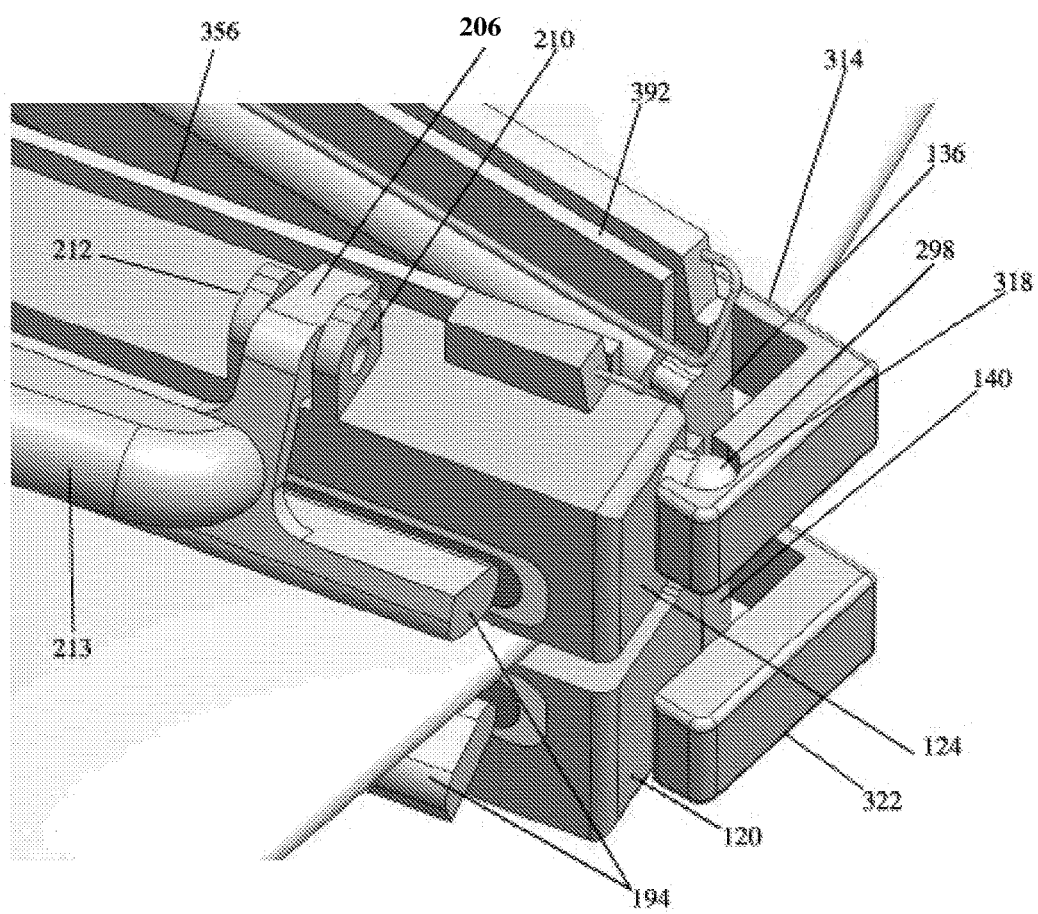
FIG. 41 is an enlarged perspective of stapler jaws and anvil jaws in the second anastomosis configuration.

The anvil 108 can be positioned over another vessel 380 to be joined to the vessel 344 in the anastomosis procedure (FIG. 32). The handles 144 and 148 are brought together to clamp the vessel 380 as indicated by the arrows in FIG. 33. The lock 280 will engage to retain the jaws 136 and 140 in the clamping position, as indicated by the arrow in FIG. 34. This will leave a clamped end 384. The clamped end 384 can be trimmed to leave a trimmed clamped end 388 of appropriate length (FIG. 35). The sides of the trimmed clamped end 388 can be cut to form flaps 392 and 396 (FIGS. 36-37). Spring arms 317 can be provided and rotated to retain the vessel flaps 392 and 396 in position (FIG. 38).

Figure 42:
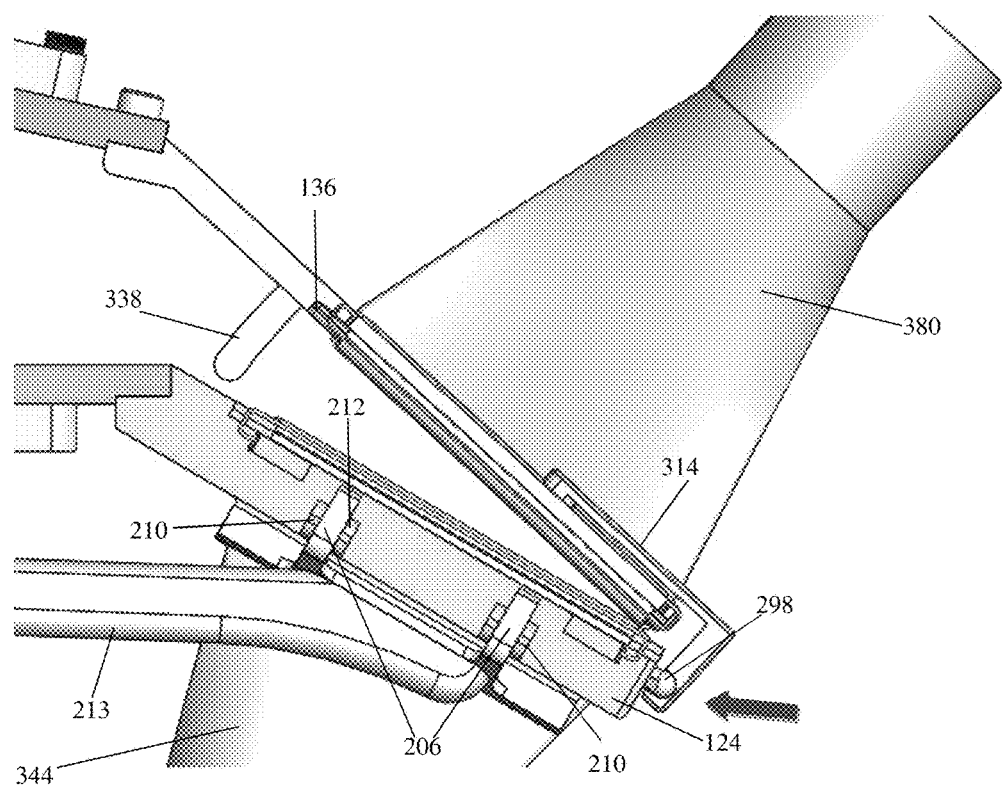
FIG. 42 is a plan elevation.
Figure 43:
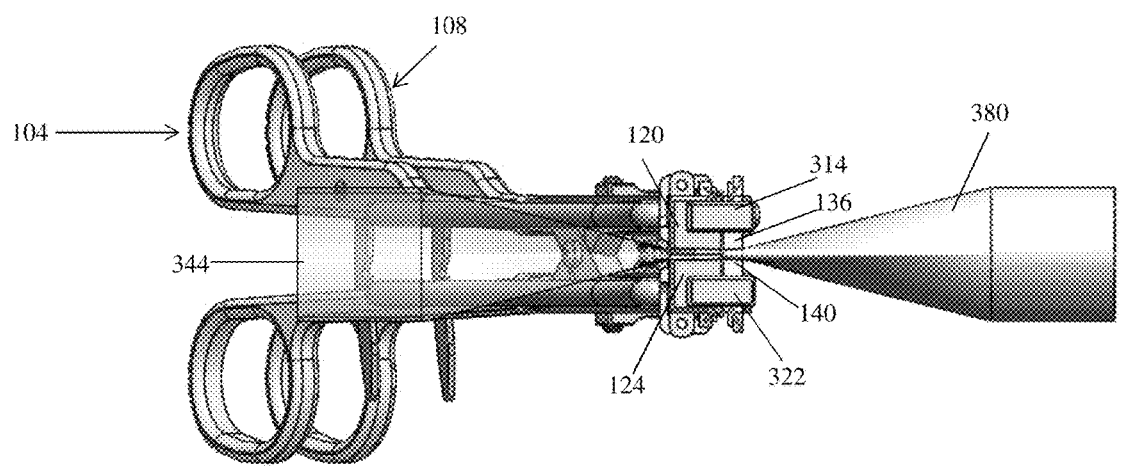
FIG. 43 is an end view, partially in phantom.
Figure 44:
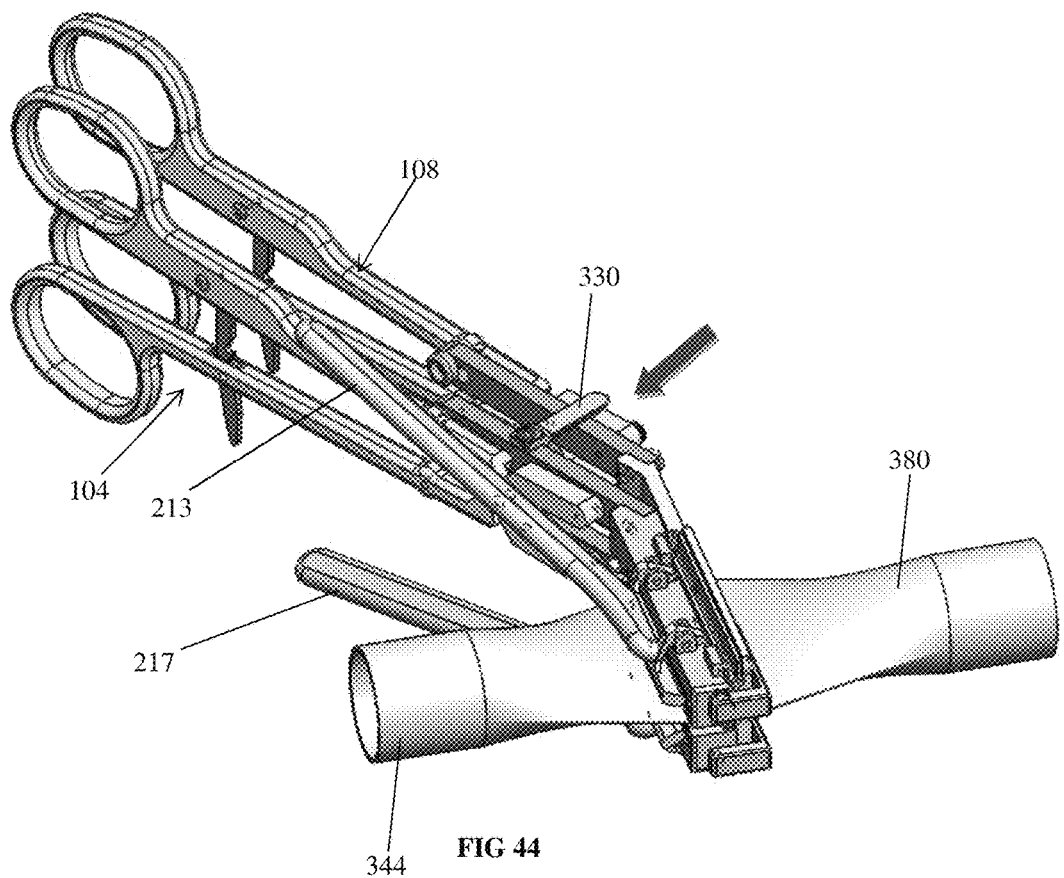
FIG. 44 is a perspective view of a stapler, anvil and vessels in a third anastomosis configuration.
Figure 45:
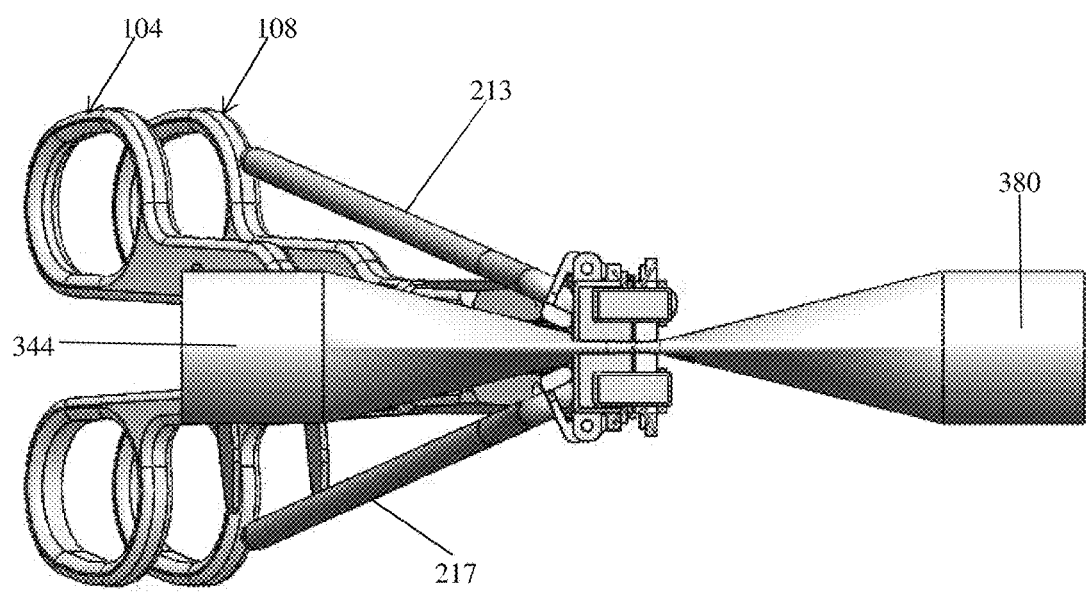
FIG. 45 is an end view.

The stapler 104 and anvil 108 with the respective clamped vessels 344 and 380 are then brought together (FIG. 39) to engage the stapler 104 to the anvil 108. The balls 298 and 300 can be engaged to the sockets 318 as indicated by the arrows in FIG. 39, although other engagement structure is possible. The balls 298 and 300 are positioned in the sockets 318, and then the respective handles of the stapler 104 and anvil 108 are brought together as indicated by the arrow in FIG. 40 and as depicted in an enlarged view in FIG. 41. The proximal portion of the stapler 104 and anvil 108 are then brought together whereupon the alignment arms 338 will engage and register with the openings 340 (FIG. 42). Further movement of the proximal portions of the stapler 104 and anvil 108 together, the catches 330 of the stapler 104 will engage the anvil 108 to further secure the stapler 104 to the anvil 108 with the staples 160 aligned with and registered to the anvil surfaces 244 (FIG. 43). The socket arms 314 and 322 being flexible, the engagement will accommodate different thicknesses of tissue.

Figure 46:
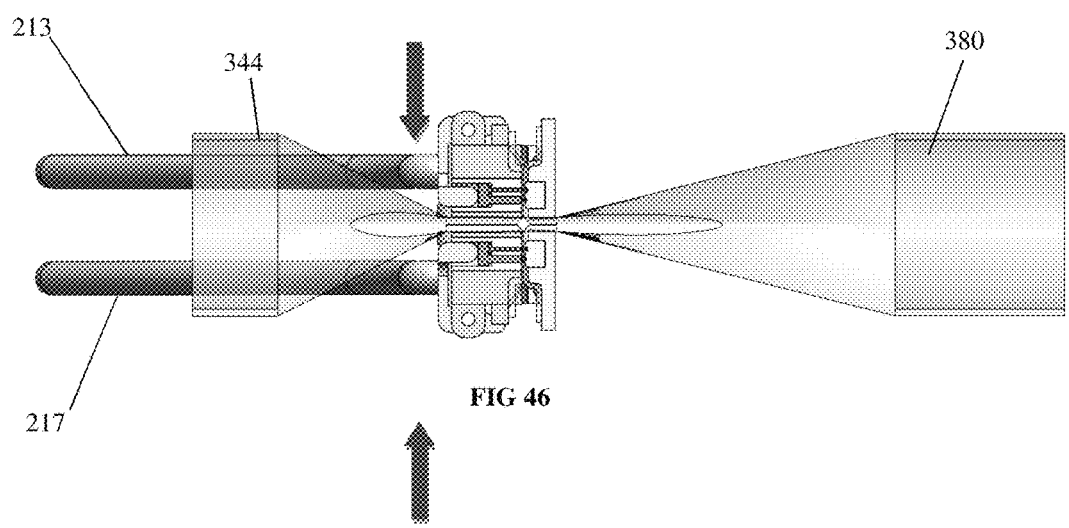
FIG. 46 is a cross-section in a fourth anastomosis configuration.
Figure 47:
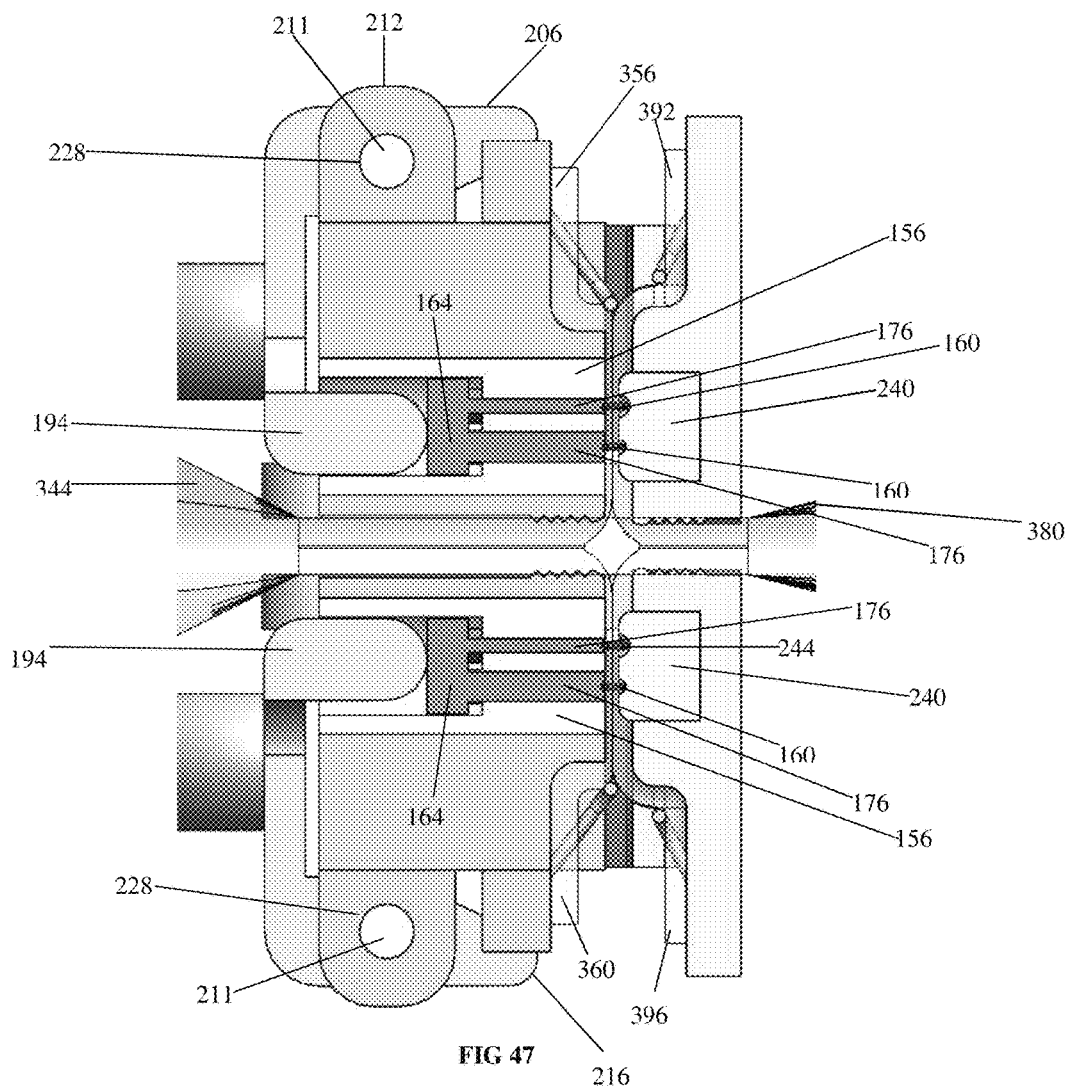
FIG. 47 is an enlarged cross-section.
Figure 48:
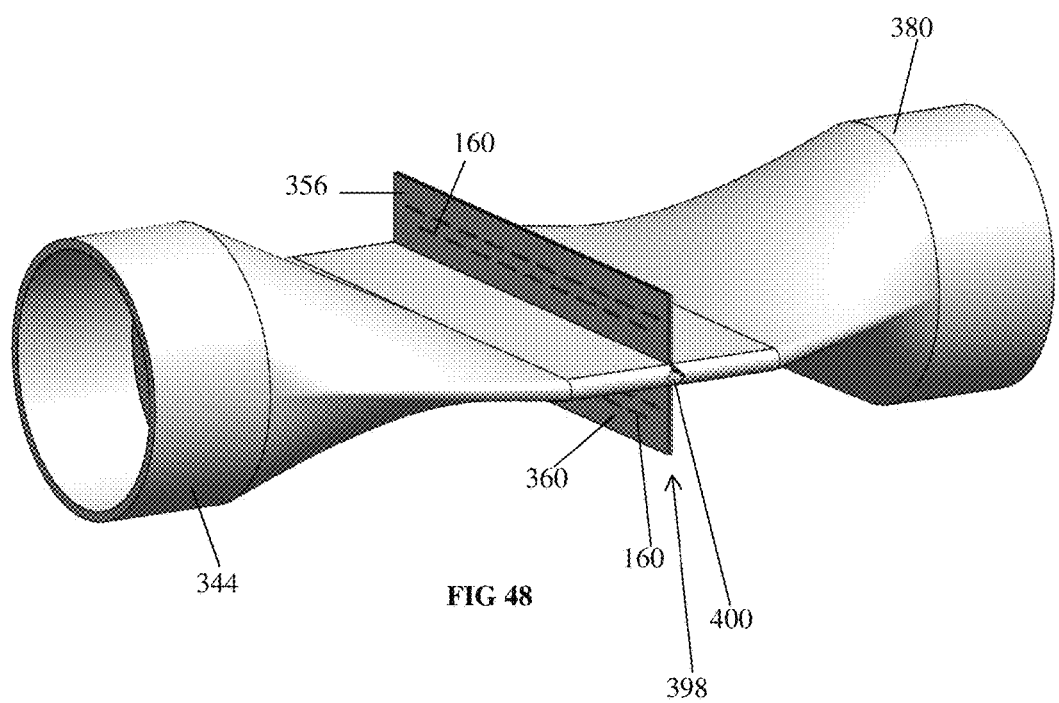
FIG. 48 is a perspective view of the anastomosed vessel.
Figure 49:
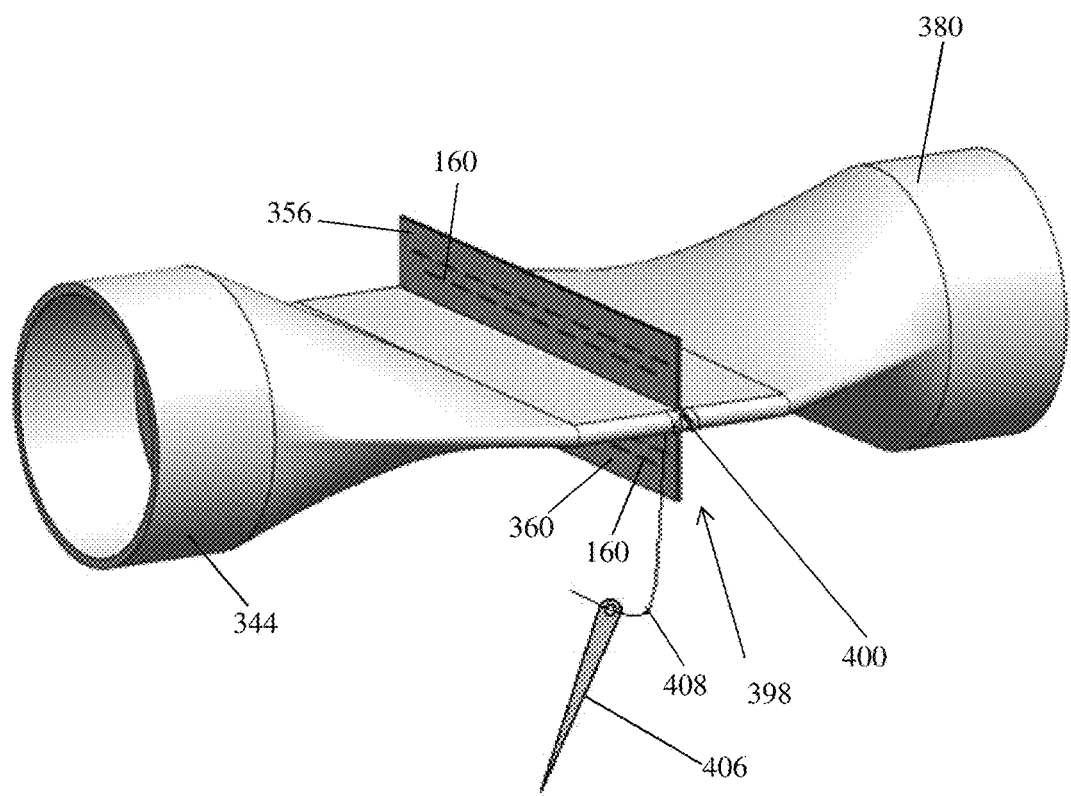
FIG. 49 is a perspective view of the anastomosed vessel and a suture needle and suture.

The levers 213 and 217 are then moved from the open position (FIGS. 44-45) to the closed position (FIG. 46). The staples 160 will be urged by the staple seats 176 upon contact between the staple plungers 194 and the staple pistons 164 (FIG. 47). The staples 160 will be driven into the anvil surfaces 244. The flaps 356 and 360 of vessel 344 will thereby be stapled to flaps 392 and 396 of the vessel 380. This will leave a linear anastomosis 398 formed by the stapling of the flaps 356 and 362 the flaps 392 and 396 of the vessel 380 (FIG. 48). This will also leave small side openings 400 at the edges of the linear anastomosis 396. The side openings 400 can be closed with conventional methods such as suturing needle 406 and suture 408, where more than one suture can be placed, or other suitable methods (FIG. 49).

The locks 270 and 280 can be released to release the clamping of the vessels 344 and 380. The latches 330 can be disengaged and the balls 298 and 300 can be disengaged from the sockets 318. The alignment arms 338 are removed from the openings 340. The stapler 104 and anvil 108 can then be removed from the surgical site.

This invention can be embodied in other forms without departing from the spirit for essential attributes thereof. Accordingly reference should be made to the following claims to determine the scope of the invention.

We claim:

1. An anastomosis device, comprising:
   a) a stapler, comprising:
      a clamp head with opposing first and second clamp jaws and a clamp actuator for moving the opposing jaws toward one another to a clamping position;
      a lock for securing the clamp jaws in the clamping position;
      a first staple magazine connected to the first clamp jaw for retaining a plurality of staples in an array, and a first driver associated with the first staple magazine for simultaneously moving the plurality of staples in the array out of the staple magazine;
      a second staple magazine connected to the second clamp jaw for retaining a plurality of staples in an array, and a second driver associated with the second staple magazine for simultaneously moving the plurality of staples in the array out of the staple magazine;
   b) an anvil, comprising:
      a clamp head with opposing first and second clamp jaws and a clamp actuator for moving the opposing jaws toward one another to a clamping position;
      a lock for securing the clamp jaws in the clamping position;
      a first anvil portion connected to the first clamp jaw;
      a second anvil portion connected to the second clamp jaw;
   c) engagement structure on the stapler and the anvil for detachable engagement of the stapler to the anvil, whereupon the first anvil portion will be positioned adjacent to and aligned with the first staple magazine and the second anvil portion will be positioned adjacent to and aligned with the second staple magazine, and the first driver associated with the first staple magazine can be operated to simultaneously move the plurality of staples from the first staple magazine into contact with the first anvil portion, and the second driver associated with the second staple magazine can be operated to simultaneously move the plurality of staples from the second staple magazine into contact with the second anvil portion.

2. The anastomosis device of claim 1, wherein the stapler comprises a handle and the anvil comprises a handle.

3. The anastomosis device of claim 1, wherein the first driver associated with the first staple magazine is connected to a first lever for operating the first driver, and the second driver associated with the second staple magazine is connected to a second lever for operating the second driver.

4. The anastomosis device of claim 1 wherein each of the first clamp jaw and second clamp jaw of the stapler and first clamp jaw and second clamp jaw of the anvil comprises tissue flap retaining members.

5. The anastomosis device of claim 4, wherein the tissue flap retaining members are spring loaded to urge the retaining member toward the respective clamp jaw.

6. The anastomosis device of claim 1, wherein the engagement structure comprises cooperating engagement structure at distal ends of the stapler and the anvil.

7. The anastomosis device of claim 6, wherein the engagement structure is cooperating ball and socket members on distal ends of the first clamp jaw of the stapler and first clamp jaw of the anvil, and cooperating ball and socket members on the second clamp jaw of the stapler and second clamp jaw of the anvil.

8. The anastomosis device of claim 1, wherein the engagement structure is adjustable to permit changes in the spacing between the first staple magazine and first anvil portion, and between the second staple magazine and the second anvil portion.

9. The anastomosis device of claim 1, wherein the first driver and second driver comprise a staple plunger.

10. The anastomosis device of claim 9, wherein the first staple magazine and second staple magazine comprise a staple piston, the staple piston being contacted and moved by the plunger to move the staples from the staple magazine.

11. The anastomosis device of claim 10, wherein each staple piston comprises plurality of individual staple seats.

12. The anastomosis device of claim 1, further comprising proximal engagement for engaging the stapler to the anvil.

13. The anastomosis device of claim 1, wherein the engagement structure comprises a latch on one of the stapler and the anvil, and a cooperating keeper on the other of the stapler and the anvil.

14. The anastomosis device of claim 1, wherein the second anvil portion and first anvil portion comprise staple anvil subportions for alignment with each of the plurality of staples in the staple array.

15. The anastomosis device of claim 1, wherein the lock for securing the clamp jaws of the stapler and the lock for securing the clamp jaws of the anvil in the clamping position comprise a ratchet.

16. The anastomosis device of claim 1, wherein the staple array comprises a linear array.

17. The anastomosis device of claim 1, wherein the staple array comprises at least two rows.

* * * * *